(12) United States Patent
Nigam et al.

(10) Patent No.: US 9,889,000 B2
(45) Date of Patent: Feb. 13, 2018

(54) CORNEAL IMPLANT APPLICATORS

(71) Applicant: ReVision Optics, Inc., Lake Forest, CA (US)

(72) Inventors: Alok Nigam, Trabuco Canyon, CA (US); Gregg Edmond Plambeck, Aliso Viejo, CA (US); Ned Schneider, Aliso Viejo, CA (US); Adam Ariely, San Diego, CA (US); David Matsuura, Encinitas, CA (US); Philip Simpson, Encinitas, CA (US)

(73) Assignee: ReVision Optics, Inc., Lake Forest, CA (US)

( * ) Notice: Subject to any disclaimer, the term of this patent is extended or adjusted under 35 U.S.C. 154(b) by 262 days.

(21) Appl. No.: 14/160,438

(22) Filed: Jan. 21, 2014

(65) Prior Publication Data

US 2014/0135915 A1    May 15, 2014

Related U.S. Application Data

(60) Continuation of application No. 13/657,650, filed on Oct. 22, 2012, now Pat. No. 8,668,735, which is a continuation-in-part of application No. 13/443,696, filed on Apr. 10, 2012, now Pat. No. 9,005,280, which is a continuation of application No. 13/206,200, filed on Aug. 9, 2011, now abandoned, which is a continuation of application No. 11/422,815, filed on Jun. 7, 2006, now Pat. No. 7,992,906, which is a continuation of application No. 11/054,639, filed on Feb. 9, 2005, now Pat. No. 7,128,351, which is a continuation of application No.
(Continued)

(51) Int. Cl.
*A61F 2/14* (2006.01)
*A61B 50/30* (2016.01)

(52) U.S. Cl.
CPC .............. *A61F 2/148* (2013.01); *A61B 50/30* (2016.02); *A61F 2/142* (2013.01); *A61F 2/1451* (2015.04)

(58) Field of Classification Search
CPC ........ A61F 2/143; A61F 2/1451; A61F 2/146; A61F 2/148; A61B 19/026
See application file for complete search history.

(56) References Cited

U.S. PATENT DOCUMENTS 2,521,161 A    9/1950    Grover
2,714,721 A    8/1955    Stone, Jr.
(Continued)

FOREIGN PATENT DOCUMENTS

DE    3208729 A1    9/1983
EP    0308077 A2    3/1989
(Continued)

OTHER PUBLICATIONS

Patel et al.; Refractive index of human corneal epithelium and stroma; J. Refract. Surg.; 11(2); Abstract; Mar. 1995 (pubmed Abstract only).
(Continued)

*Primary Examiner* — Julie A Szpira
(74) *Attorney, Agent, or Firm* — Shay Glenn LLP

(57) ABSTRACT

Devices and methods for handling and depositing corneal implants onto corneal tissue. Devices and methods for packaging and storing corneal implants.

4 Claims, 37 Drawing Sheets

Related U.S. Application Data

10/463,091, filed on Jun. 17, 2003, now Pat. No. 6,893,461, which is a division of application No. 09/843,547, filed on Apr. 26, 2001, now Pat. No. 6,581,993, which is a continuation-in-part of application No. 09/660,371, filed on Sep. 12, 2000, now Pat. No. 6,543,610.

(60) Provisional application No. 61/550,185, filed on Oct. 21, 2011, provisional application No. 61/679,482, filed on Aug. 3, 2012, provisional application No. 61/606,674, filed on Mar. 5, 2012.

(56) References Cited

U.S. PATENT DOCUMENTS

| | | |
|---|---|---|
| 3,091,328 A * | 5/1963 | Leonardos .......... A45C 11/005 134/156 |
| 3,168,100 A | 2/1965 | Rich |
| 3,343,657 A | 9/1967 | Speshyock |
| 3,379,200 A | 4/1968 | Pennell |
| 3,482,906 A | 12/1969 | Volk |
| 3,743,337 A | 7/1973 | Crary |
| 3,770,113 A | 11/1973 | Thomas |
| 3,879,076 A | 4/1975 | Barnett |
| 3,950,315 A | 4/1976 | Cleaver |
| 3,996,627 A | 12/1976 | Deeg et al. |
| 4,030,480 A | 6/1977 | Meyer |
| 4,037,604 A | 7/1977 | Newkirk |
| 4,039,827 A | 8/1977 | Zdrok et al. |
| 4,065,816 A | 1/1978 | Sawyer |
| 4,071,272 A | 1/1978 | Drdlik |
| 4,093,291 A * | 6/1978 | Schurgin .......... A61F 9/0061 294/1.2 |
| 4,136,406 A | 1/1979 | Norris |
| 4,157,718 A | 6/1979 | Baehr |
| 4,184,491 A | 1/1980 | McGannon |
| 4,194,814 A | 3/1980 | Fischer et al. |
| 4,238,524 A | 12/1980 | LaLiberte et al. |
| 4,257,521 A * | 3/1981 | Poler .......... A61F 2/1691 206/205 |
| 4,263,054 A * | 4/1981 | Giambalvo .......... A45C 11/005 134/21 |
| 4,268,133 A | 5/1981 | Fischer et al. |
| 4,326,306 A | 4/1982 | Poler |
| 4,357,940 A | 11/1982 | Muller |
| 4,392,569 A | 7/1983 | Shoup |
| 4,418,991 A | 12/1983 | Breger |
| 4,423,809 A | 1/1984 | Mazzocco |
| 4,428,746 A | 1/1984 | Mendez |
| 4,452,235 A | 6/1984 | Reynolds |
| 4,466,705 A | 8/1984 | Michelson |
| 4,490,860 A | 1/1985 | Rainin |
| 4,504,982 A | 3/1985 | Burk |
| 4,521,210 A | 6/1985 | Wong |
| 4,525,044 A | 6/1985 | Bauman |
| 4,545,478 A | 10/1985 | Waldman |
| 4,554,115 A | 11/1985 | Neefe |
| 4,554,918 A | 11/1985 | White |
| 4,565,198 A | 1/1986 | Koeniger |
| 4,573,998 A | 3/1986 | Mazzocco |
| 4,580,882 A | 4/1986 | Nuchman et al. |
| 4,586,929 A | 5/1986 | Binder |
| 4,604,087 A | 8/1986 | Joseph |
| 4,607,617 A | 8/1986 | Choyce |
| 4,616,910 A | 10/1986 | Klein |
| 4,618,227 A | 10/1986 | Bayshore |
| 4,619,256 A | 10/1986 | Horn |
| 4,624,664 A | 11/1986 | Peluso et al. |
| 4,624,669 A | 11/1986 | Grendahl |
| 4,640,595 A | 2/1987 | Volk |
| 4,646,720 A | 3/1987 | Peyman et al. |
| 4,655,774 A | 4/1987 | Choyce |
| 4,662,370 A | 5/1987 | Hoffmann et al. |
| 4,663,358 A | 5/1987 | Hyon et al. |
| 4,671,276 A | 6/1987 | Reynolds |
| 4,676,792 A | 6/1987 | Praeger |
| 4,697,697 A | 10/1987 | Graham et al. |
| 4,702,244 A | 10/1987 | Mazzocco |
| 4,709,697 A | 12/1987 | Muller |
| 4,721,124 A | 1/1988 | Tuerkheimer et al. |
| 4,726,367 A | 2/1988 | Shoemaker |
| 4,750,901 A | 6/1988 | Molteno |
| 4,762,496 A | 8/1988 | Maloney et al. |
| 4,766,895 A | 8/1988 | Reynolds |
| 4,769,033 A | 9/1988 | Nordan |
| 4,772,283 A | 9/1988 | White |
| 4,778,462 A | 10/1988 | Grendahl |
| 4,798,609 A | 1/1989 | Grendahl |
| 4,806,382 A | 2/1989 | Goldberg et al. |
| 4,836,201 A | 6/1989 | Patton et al. |
| 4,840,175 A | 6/1989 | Peyman |
| 4,842,599 A | 6/1989 | Bronstein |
| 4,844,242 A | 7/1989 | Chen et al. |
| 4,851,003 A | 7/1989 | Lindstrom |
| 4,860,885 A | 8/1989 | Kaufman et al. |
| 4,865,552 A | 9/1989 | Maloney et al. |
| 4,886,488 A | 12/1989 | White |
| 4,888,016 A | 12/1989 | Langerman |
| 4,897,981 A | 2/1990 | Beck |
| 4,911,715 A | 3/1990 | Kelman |
| 4,919,130 A | 4/1990 | Stoy et al. |
| 4,923,467 A | 5/1990 | Thompson |
| 4,934,363 A | 6/1990 | Smith et al. |
| 4,936,825 A | 6/1990 | Ungerleider |
| 4,946,436 A | 8/1990 | Smith |
| 4,955,903 A | 9/1990 | Sulc et al. |
| 4,968,296 A | 11/1990 | Ritch et al. |
| 4,971,732 A | 11/1990 | Wichterle |
| 4,976,719 A | 12/1990 | Siepser |
| 5,019,084 A | 5/1991 | Aysta et al. |
| 5,019,098 A | 5/1991 | Mercier |
| 5,022,414 A | 6/1991 | Muller |
| 5,030,230 A | 7/1991 | White |
| 5,041,081 A | 8/1991 | Odrich |
| 5,063,942 A | 11/1991 | Kilmer et al. |
| 5,071,276 A | 12/1991 | Nielsen et al. |
| 5,073,163 A | 12/1991 | Lippman |
| 5,092,837 A | 3/1992 | Ritch et al. |
| 5,098,444 A | 3/1992 | Feaster |
| 5,108,428 A | 4/1992 | Capecchi et al. |
| 5,112,350 A | 5/1992 | Civerchia et al. |
| 5,123,905 A | 6/1992 | Kelman |
| 5,123,912 A | 6/1992 | Kaplan et al. |
| 5,123,921 A | 6/1992 | Werblin et al. |
| 5,139,518 A | 8/1992 | White |
| 5,163,934 A | 11/1992 | Munnerlyn |
| 5,171,213 A | 12/1992 | Price, Jr. |
| 5,173,723 A | 12/1992 | Volk |
| 5,178,604 A | 1/1993 | Baerveldt et al. |
| 5,180,362 A | 1/1993 | Worst et al. |
| 5,181,053 A | 1/1993 | Brown |
| 5,188,125 A | 2/1993 | Kilmer et al. |
| 5,190,552 A | 3/1993 | Kelman |
| 5,192,317 A | 3/1993 | Kalb |
| 5,196,026 A | 3/1993 | Barrett et al. |
| 5,211,660 A | 5/1993 | Grasso |
| 5,225,858 A | 7/1993 | Portney |
| 5,229,797 A | 7/1993 | Futhey et al. |
| 5,244,799 A | 9/1993 | Anderson |
| 5,258,042 A | 11/1993 | Mehta |
| 5,270,744 A | 12/1993 | Portnoy |
| 5,273,750 A | 12/1993 | Homiger et al. |
| 5,282,851 A | 2/1994 | Jacob-LaBarre |
| 5,300,020 A | 4/1994 | L'Esperance, Jr. |
| 5,300,116 A | 4/1994 | Chirila et al. |
| 5,312,413 A | 5/1994 | Eaton et al. |
| 5,318,044 A | 6/1994 | Kilmer et al. |
| 5,318,046 A | 6/1994 | Rozakis |
| 5,318,047 A | 6/1994 | Davenport et al. |
| 5,336,261 A | 8/1994 | Barrett et al. |
| 5,338,291 A | 8/1994 | Speckman et al. |
| 5,344,448 A | 9/1994 | Schneider et al. |
| 5,346,464 A | 9/1994 | Camras |

(56) References Cited

U.S. PATENT DOCUMENTS

| | | |
|---|---|---|
| 5,352,233 A | 10/1994 | Anis |
| 5,370,607 A | 12/1994 | Memmen |
| 5,372,577 A | 12/1994 | Ungerleider |
| 5,385,582 A | 1/1995 | Ommaya |
| 5,391,201 A | 2/1995 | Barrett et al. |
| 5,397,300 A | 3/1995 | Baerveldt et al. |
| 5,405,384 A | 4/1995 | Silvestrini |
| 5,407,241 A | 4/1995 | Harrison |
| 5,428,412 A | 6/1995 | Stoyan |
| 5,433,701 A | 7/1995 | Rubinstein |
| 5,454,796 A | 10/1995 | Krupin |
| 5,458,819 A | 10/1995 | Chirila et al. |
| 5,467,149 A | 11/1995 | Morrison et al. |
| 5,474,562 A | 12/1995 | Orchowski et al. |
| 5,476,445 A | 12/1995 | Baerveldt et al. |
| 5,487,377 A | 1/1996 | Smith et al. |
| 5,489,301 A | 2/1996 | Barber |
| 5,493,350 A | 2/1996 | Seidner |
| 5,502,518 A | 3/1996 | Lieberman |
| 5,512,220 A | 4/1996 | Roffman et al. |
| 5,520,631 A | 5/1996 | Nordquist et al. |
| 5,521,656 A | 5/1996 | Portney |
| 5,530,491 A | 6/1996 | Baude et al. |
| 5,533,997 A | 7/1996 | Ruiz |
| 5,570,142 A | 10/1996 | Lieberman |
| 5,591,185 A | 1/1997 | Kilmer et al. |
| 5,598,234 A | 1/1997 | Blum et al. |
| 5,601,584 A | 2/1997 | Obagi et al. |
| 5,616,148 A | 4/1997 | Eagles et al. |
| 5,620,450 A | 4/1997 | Eagles et al. |
| 5,628,794 A | 5/1997 | Lindstrom |
| 5,630,810 A | 5/1997 | Machat |
| 5,634,943 A | 6/1997 | Villain et al. |
| 5,643,276 A | 7/1997 | Zaleski |
| 5,647,865 A | 7/1997 | Swinger |
| 5,657,108 A | 8/1997 | Portney |
| 5,682,223 A | 10/1997 | Menezes et al. |
| 5,684,560 A | 11/1997 | Roffman et al. |
| 5,715,031 A | 2/1998 | Roffman et al. |
| 5,716,633 A | 2/1998 | Civerchia |
| 5,722,948 A | 3/1998 | Gross |
| 5,722,971 A | 3/1998 | Peyman |
| 5,728,155 A | 3/1998 | Anello et al. |
| 5,732,990 A | 3/1998 | Yavitz et al. |
| 5,752,928 A | 5/1998 | de Roulhac et al. |
| 5,755,785 A | 5/1998 | Rowsey et al. |
| 5,766,181 A | 6/1998 | Chambers et al. |
| 5,772,667 A | 6/1998 | Blake |
| 5,779,711 A | 7/1998 | Kritzinger et al. |
| 5,785,674 A | 7/1998 | Mateen |
| 5,800,442 A | 9/1998 | Wolf et al. |
| 5,800,529 A | 9/1998 | Brauker et al. |
| 5,805,260 A | 9/1998 | Roffman et al. |
| 5,810,833 A | 9/1998 | Brady et al. |
| 5,817,115 A | 10/1998 | Nigam |
| 5,824,086 A | 10/1998 | Silvestrini |
| 5,847,802 A | 12/1998 | Menezes et al. |
| 5,855,604 A | 1/1999 | Lee |
| 5,860,984 A | 1/1999 | Chambers et al. |
| 5,872,613 A | 2/1999 | Blum et al. |
| 5,873,889 A | 2/1999 | Chin |
| 5,876,439 A | 3/1999 | Lee |
| 5,888,243 A | 3/1999 | Silvestrini |
| 5,893,719 A | 4/1999 | Radow |
| 5,913,898 A | 6/1999 | Feingold |
| 5,919,185 A | 7/1999 | Peyman |
| 5,928,245 A | 7/1999 | Wolf et al. |
| 5,929,968 A | 7/1999 | Cotie et al. |
| 5,929,969 A | 7/1999 | Roffman |
| 5,935,140 A | 8/1999 | Buratto |
| 5,941,583 A | 8/1999 | Raimondi |
| 5,944,752 A | 8/1999 | Silvestrini |
| 5,945,498 A | 8/1999 | Hopken et al. |
| 5,964,748 A | 10/1999 | Peyman |
| 5,964,776 A | 10/1999 | Peyman |
| 5,968,065 A | 10/1999 | Chin |
| 5,976,150 A | 11/1999 | Copeland |
| 5,976,168 A | 11/1999 | Chin |
| 5,980,549 A | 11/1999 | Chin |
| 6,007,510 A | 12/1999 | Nigam |
| 6,010,510 A | 1/2000 | Brown et al. |
| 6,024,448 A | 2/2000 | Wu et al. |
| 6,033,395 A | 3/2000 | Peyman |
| 6,036,714 A | 3/2000 | Chin |
| 6,050,999 A * | 4/2000 | Paraschac ............... A61F 2/148 |
| | | 219/636 |
| 6,055,990 A | 5/2000 | Thompson |
| 6,059,775 A | 5/2000 | Nielsen |
| 6,066,170 A | 5/2000 | Lee |
| 6,068,642 A | 5/2000 | Johnson et al. |
| 6,079,826 A | 6/2000 | Appleton et al. |
| 6,083,231 A | 7/2000 | Van Noy et al. |
| 6,086,202 A | 7/2000 | Chateau et al. |
| 6,090,141 A | 7/2000 | Lindstrom |
| 6,102,946 A | 8/2000 | Nigam |
| 6,110,166 A | 8/2000 | Juhasz et al. |
| 6,120,148 A | 9/2000 | Fiala et al. |
| 6,125,294 A | 9/2000 | Scholl et al. |
| 6,129,733 A | 10/2000 | Brady et al. |
| 6,139,560 A | 10/2000 | Kremer |
| 6,142,969 A | 11/2000 | Nigam |
| 6,143,001 A | 11/2000 | Brown et al. |
| 6,159,241 A | 12/2000 | Lee et al. |
| 6,171,324 B1 | 1/2001 | Cote et al. |
| 6,175,754 B1 | 1/2001 | Scholl et al. |
| RE37,071 E | 2/2001 | Gabrielian et al. |
| 6,183,513 B1 | 2/2001 | Guenthner et al. |
| 6,197,019 B1 | 3/2001 | Peyman |
| 6,197,057 B1 | 3/2001 | Peyman et al. |
| 6,197,058 B1 | 3/2001 | Portney |
| 6,203,538 B1 | 3/2001 | Peyman |
| 6,203,549 B1 | 3/2001 | Waldock |
| 6,203,557 B1 | 3/2001 | Chin |
| 6,206,919 B1 | 3/2001 | Lee |
| 6,210,005 B1 | 4/2001 | Portney |
| 6,214,015 B1 | 4/2001 | Reich et al. |
| 6,214,044 B1 | 4/2001 | Silverstrini |
| 6,217,571 B1 | 4/2001 | Peyman |
| 6,221,067 B1 | 4/2001 | Peyman |
| 6,228,113 B1 | 5/2001 | Kaufman |
| 6,228,114 B1 | 5/2001 | Lee |
| 6,248,111 B1 | 6/2001 | Glick et al. |
| 6,250,757 B1 | 6/2001 | Roffman et al. |
| 6,251,114 B1 | 6/2001 | Farmer et al. |
| 6,264,648 B1 | 7/2001 | Peyman |
| 6,264,670 B1 | 7/2001 | Chin |
| 6,264,692 B1 | 7/2001 | Woffinden et al. |
| 6,267,768 B1 | 7/2001 | Deacon et al. |
| 6,271,281 B1 | 8/2001 | Liao et al. |
| 6,277,137 B1 | 8/2001 | Chin |
| 6,280,449 B1 * | 8/2001 | Blake .................... A61F 2/1664 |
| | | 606/107 |
| 6,280,470 B1 | 8/2001 | Peyman |
| 6,283,595 B1 | 9/2001 | Breger |
| 6,302,877 B1 | 10/2001 | Ruiz |
| 6,325,509 B1 | 12/2001 | Hodur et al. |
| 6,325,792 B1 | 12/2001 | Swinger et al. |
| 6,350,272 B1 | 2/2002 | Kawesch |
| 6,361,560 B1 | 3/2002 | Nigam |
| 6,364,483 B1 | 4/2002 | Grossinger et al. |
| 6,371,960 B2 | 4/2002 | Heyman et al. |
| 6,391,230 B1 | 5/2002 | Sarbadhikari |
| 6,398,277 B1 | 6/2002 | McDonald |
| 6,398,789 B1 | 6/2002 | Capetan |
| 6,428,572 B2 | 8/2002 | Nagai |
| 6,435,681 B2 | 8/2002 | Portney |
| 6,436,092 B1 | 8/2002 | Peyman |
| 6,447,519 B1 | 9/2002 | Brady et al. |
| 6,447,520 B1 | 9/2002 | Ott et al. |
| 6,458,141 B1 | 10/2002 | Peyman |
| 6,461,384 B1 | 10/2002 | Hoffmann et al. |
| 6,471,708 B2 | 10/2002 | Green |
| 6,474,814 B1 | 11/2002 | Griffin |
| 6,506,200 B1 | 1/2003 | Chin |

(56) References Cited

U.S. PATENT DOCUMENTS

| | | |
|---|---|---|
| 6,511,178 B1 | 1/2003 | Roffman et al. |
| 6,527,389 B2 | 3/2003 | Portney |
| 6,537,283 B2 | 3/2003 | Van Noy |
| 6,543,610 B1 | 4/2003 | Nigam |
| 6,544,286 B1 | 4/2003 | Perez |
| 6,551,307 B2 | 4/2003 | Peyman |
| 6,554,424 B1 | 4/2003 | Miller et al. |
| 6,554,425 B1 | 4/2003 | Roffman et al. |
| 6,557,998 B2 | 5/2003 | Portney |
| 6,581,993 B2 | 6/2003 | Nigam |
| 6,582,076 B1 | 6/2003 | Roffman et al. |
| 6,589,057 B1 | 7/2003 | Keenan et al. |
| 6,589,203 B1 | 7/2003 | Mitrev |
| 6,589,280 B1 | 7/2003 | Koziol |
| 6,592,591 B2 | 7/2003 | Polla et al. |
| 6,596,000 B2 | 7/2003 | Chan et al. |
| 6,605,093 B1 | 8/2003 | Blake |
| 6,607,537 B1 | 8/2003 | Binder |
| 6,607,556 B1 | 8/2003 | Nigam |
| 6,623,522 B2 | 9/2003 | Nigam |
| 6,626,941 B2 | 9/2003 | Nigam |
| 6,629,979 B1 | 10/2003 | Feingold et al. |
| 6,632,244 B1 | 10/2003 | Nigam |
| 6,641,577 B2 | 11/2003 | Bille |
| 6,645,246 B1 | 11/2003 | Weinschenk, III et al. |
| 6,648,877 B1 | 11/2003 | Juhasz et al. |
| 6,657,029 B2 | 12/2003 | Vanderbilt |
| 6,666,887 B1 | 12/2003 | Callahan et al. |
| 6,673,112 B2 | 1/2004 | Nigam |
| 6,702,807 B2 | 3/2004 | Peyman |
| 6,709,103 B1 | 3/2004 | Roffman et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,733,526 B2 | 5/2004 | Paul et al. |
| 6,740,078 B2 | 5/2004 | Tamayo |
| 6,808,262 B2 | 10/2004 | Chapoy et al. |
| 6,824,178 B2 | 11/2004 | Nigam |
| 6,849,090 B2 | 2/2005 | Nigam |
| 6,855,163 B2 | 2/2005 | Peyman |
| 6,875,232 B2 | 4/2005 | Nigam |
| 6,879,402 B2 | 4/2005 | Küchel |
| 6,881,197 B1 | 4/2005 | Nigam |
| 6,893,461 B2 | 5/2005 | Nigam |
| 6,949,093 B1 | 9/2005 | Peyman |
| 6,955,432 B2 * | 10/2005 | Graham ............... A61F 9/0061 294/1.2 |
| 7,128,351 B2 | 10/2006 | Nigam |
| 7,585,075 B2 | 9/2009 | Marmo |
| 7,699,837 B2 | 4/2010 | Cox et al. |
| 7,776,086 B2 | 8/2010 | Miller |
| 7,976,577 B2 | 7/2011 | Silvestrini |
| 7,992,906 B2 | 8/2011 | Nigam |
| 8,057,541 B2 | 11/2011 | Dishler et al. |
| 8,162,953 B2 | 4/2012 | Dishler et al. |
| 8,469,948 B2 | 6/2013 | Dishler et al. |
| 8,540,727 B2 | 9/2013 | Dishler et al. |
| 8,668,735 B2 | 3/2014 | Nigam et al. |
| 8,685,292 B2 | 4/2014 | Mandler et al. |
| 2001/0027314 A1 | 10/2001 | Peyman |
| 2001/0031959 A1 | 10/2001 | Rozakis et al. |
| 2001/0051826 A1 | 12/2001 | Bogaert et al. |
| 2002/0010510 A1 | 1/2002 | Silvestrini |
| 2002/0055753 A1 | 5/2002 | Silvestrini |
| 2002/0063068 A1 | 5/2002 | Faxe |
| 2002/0101563 A1 | 8/2002 | Miyamura et al. |
| 2002/0103538 A1 | 8/2002 | Hughes et al. |
| 2002/0138069 A1 | 9/2002 | Peyman |
| 2003/0014042 A1 | 1/2003 | Juhasz et al. |
| 2003/0033010 A1 | 2/2003 | Hicks et al. |
| 2003/0069637 A1 | 4/2003 | Lynch et al. |
| 2003/0078487 A1 | 4/2003 | Jeffries et al. |
| 2003/0176855 A1 | 9/2003 | Gross et al. |
| 2003/0204252 A1 * | 10/2003 | Paul ...................... A61F 2/0095 623/5.16 |
| 2003/0208190 A1 | 11/2003 | Roberts et al. |
| 2003/0220653 A1 | 11/2003 | Perez |
| 2003/0229303 A1 | 12/2003 | Haffner et al. |
| 2004/0010278 A1 | 1/2004 | Nakamura et al. |
| 2004/0019379 A1 | 1/2004 | Glick et al. |
| 2004/0034413 A1 | 2/2004 | Christensen |
| 2004/0054408 A1 | 3/2004 | Glick et al. |
| 2004/0059320 A1 | 3/2004 | Telandro et al. |
| 2004/0073303 A1 | 4/2004 | Schanzlin |
| 2005/0080484 A1 | 4/2005 | Marmo et al. |
| 2005/0080485 A1 | 4/2005 | Nigam |
| 2005/0113844 A1 | 5/2005 | Nigam |
| 2005/0119738 A1 | 6/2005 | Nigam |
| 2005/0143717 A1 | 6/2005 | Peyman |
| 2005/0178394 A1 | 8/2005 | Slade |
| 2005/0182350 A1 | 8/2005 | Nigam |
| 2005/0182488 A1 | 8/2005 | Peyman |
| 2005/0203494 A1 | 9/2005 | Holliday |
| 2005/0222679 A1 | 10/2005 | Peyman |
| 2005/0246016 A1 | 11/2005 | Miller et al. |
| 2005/0261752 A1 | 11/2005 | Chernyak |
| 2006/0004381 A1 | 1/2006 | Feingold et al. |
| 2006/0020267 A1 | 1/2006 | Marmo |
| 2006/0105309 A1 | 5/2006 | Stoll et al. |
| 2006/0116762 A1 | 6/2006 | Hong et al. |
| 2006/0134170 A1 | 6/2006 | Griffith et al. |
| 2006/0142780 A1 | 6/2006 | Pynson et al. |
| 2006/0142781 A1 | 6/2006 | Pynson et al. |
| 2006/0173539 A1 | 8/2006 | Shiuey |
| 2006/0235430 A1 | 10/2006 | Le et al. |
| 2007/0027538 A1 | 2/2007 | Aharoni et al. |
| 2007/0038276 A1 | 2/2007 | Yaldo |
| 2007/0106318 A1 | 5/2007 | McDonald |
| 2007/0106376 A1 | 5/2007 | Roberts et al. |
| 2007/0129797 A1 | 6/2007 | Lang et al. |
| 2007/0182920 A1 | 8/2007 | Back et al. |
| 2007/0244559 A1 | 10/2007 | Shiuey |
| 2007/0255401 A1 | 11/2007 | Lang |
| 2007/0270945 A1 | 11/2007 | Kobayashi et al. |
| 2007/0280994 A1 | 12/2007 | Cunanan |
| 2008/0039825 A1 | 2/2008 | Lai et al. |
| 2008/0228177 A1 | 9/2008 | Moritz et al. |
| 2008/0262610 A1 | 10/2008 | Lang et al. |
| 2008/0269771 A1 | 10/2008 | Fulcher |
| 2008/0275433 A1 | 11/2008 | Russmann et al. |
| 2008/0281304 A1 | 11/2008 | Campbell |
| 2009/0005764 A1 | 1/2009 | Knox et al. |
| 2009/0079940 A1 | 3/2009 | Dai et al. |
| 2009/0198325 A1 | 8/2009 | Holliday et al. |
| 2009/0216217 A1 | 8/2009 | Odrich et al. |
| 2009/0326650 A1 | 12/2009 | Zickler et al. |
| 2010/0069915 A1 | 3/2010 | Shiuey |
| 2010/0210996 A1 | 8/2010 | Peyman |
| 2010/0241060 A1 | 9/2010 | Roizman et al. |
| 2010/0331830 A1 | 12/2010 | Bischoff et al. |
| 2010/0331831 A1 | 12/2010 | Bischoff et al. |
| 2011/0029073 A1 | 2/2011 | Liang |
| 2011/0149241 A1 | 6/2011 | Dai |
| 2011/0172675 A1 | 7/2011 | Danta et al. |
| 2011/0208300 A1 | 8/2011 | de Juan et al. |
| 2011/0218623 A1 | 9/2011 | Dishler et al. |
| 2011/0256806 A1 | 10/2011 | Monnoyeur |
| 2011/0290681 A1 | 12/2011 | Nigam |
| 2011/0319876 A1 | 12/2011 | Feingold |
| 2012/0203238 A1 | 8/2012 | Nigam |
| 2012/0231416 A1 | 9/2012 | Drapeau et al. |
| 2012/0238806 A1 | 9/2012 | Mangiardi et al. |
| 2012/0245592 A1 | 9/2012 | Berner et al. |
| 2013/0023892 A1 | 1/2013 | Schneider et al. |
| 2013/0060255 A1 | 3/2013 | Feingold et al. |
| 2013/0211523 A1 | 8/2013 | Southard et al. |
| 2013/0231739 A1 | 9/2013 | Dishler et al. |
| 2013/0253527 A1 | 9/2013 | Schneider et al. |
| 2013/0253529 A1 | 9/2013 | Walter et al. |
| 2013/0281993 A1 | 10/2013 | Dishler et al. |
| 2013/0317605 A1 | 11/2013 | Ide et al. |
| 2013/0331935 A1 | 12/2013 | Krause et al. |
| 2014/0257477 A1 | 9/2014 | Plambeck et al. |
| 2014/0288540 A1 | 9/2014 | Bischoff et al. |

(56) References Cited

U.S. PATENT DOCUMENTS

| | | |
|---|---|---|
| 2015/0080865 A1 | 3/2015 | Holliday et al. |
| 2016/0184085 A1 | 6/2016 | Schneider et al. |
| 2016/0331517 A1 | 11/2016 | Dishler et al. |
| 2017/0128193 A1 | 5/2017 | Schneider et al. |
| 2017/0143544 A1 | 5/2017 | Holliday et al. |

FOREIGN PATENT DOCUMENTS

| | | |
|---|---|---|
| EP | 0420549 A2 | 4/1991 |
| EP | 0729323 B1 | 7/1998 |
| EP | 0668061 B1 | 9/2000 |
| JP | S5973622 A | 4/1984 |
| JP | 01-195853 | 8/1989 |
| JP | 02-211119 | 8/1990 |
| JP | 5502811 | 5/1993 |
| JP | H06510687 | 12/1994 |
| JP | 08-501009 | 2/1996 |
| JP | 9-504706 | 5/1997 |
| JP | 2000506056 | 5/2000 |
| JP | 2001091910 A | 4/2001 |
| JP | 2002537895 | 11/2002 |
| JP | 03-508135 | 3/2003 |
| JP | 2007500070 | 1/2007 |
| JP | 2010507814 A | 3/2010 |
| JP | 2010220488 A | 10/2010 |
| JP | 2012523854 A | 10/2012 |
| KR | 2001-0013218 | 2/2001 |
| RU | 2294722 C2 | 3/2007 |
| WO | WO92/08423 A1 | 5/1992 |
| WO | WO93/05731 A1 | 4/1993 |
| WO | WO96/26690 A1 | 9/1996 |
| WO | WO 98/08549 A1 | 3/1998 |
| WO | WO 98/48715 A1 | 11/1998 |
| WO | WO 99/17691 A1 | 4/1999 |
| WO | WO 99/21513 A1 | 5/1999 |
| WO | WO 99/30645 A2 | 6/1999 |
| WO | WO 00/38594 A1 | 7/2000 |
| WO | WO 03/041616 A1 | 5/2003 |
| WO | WO 03/061518 A2 | 7/2003 |
| WO | WO 03/101341 A2 | 12/2003 |
| WO | WO 2005/020792 A2 | 3/2005 |
| WO | WO 2005/107648 A2 | 11/2005 |
| WO | WO 2006/029316 A1 | 4/2006 |
| WO | WO 2006/060363 A2 | 6/2006 |
| WO | WO 2007/101016 A2 | 9/2007 |
| WO | WO 2007/132332 A2 | 11/2007 |
| WO | WO2010/084595 A1 | 7/2010 |
| WO | WO2011/069907 A1 | 6/2011 |

OTHER PUBLICATIONS

Esguerra et al.; U.S. Appl. No. 14/463,355 entitled "Corneal implant storage, packaging, and delivery devices," filed Aug. 19, 2014.
Alio, J. J., et al., "Intracorneal Inlay Complicated by Intrastomal Epithelial Opacification," Arch Ophthalmol, Oct. 2004; vol. 122; 6 pages.
Cheng, et al.; "Predicting subjective judgment of best focus with objective image quality metrics"; Journal of Vision; Apr. 23, 2004; vol. 4(4); pp. 310-321.
Churms, P.W., "The Theory and Computation of Optical Modifications to the Cornea in Refractive Keratoplasty," American Journal of Optometry & Physiological Optics, 56:2, pp. 67-74, Feb. 1979.
Huang et al.; Mathematical Model of Corneal Surface Smoothing After Laser Refractive Surgery; American Journal of Ophthalmology; Mar. 2003; pp. 267-278.
Lang, A.J. et al., "First order design of intracorneal inlays: dependence on keratometric flap and corneal properties," ARVO Abstracts 2006, poster No. 3591, May 3, 2006.
Liou, H. L. et al., "Anatomically accurate, finite model eye for optical modeling", Journal of the Optical Society of America, vol. 14, No. 8, Aug. 1997.
Marsack,et al.; "Metrics of optical quality derived from wave aberrations predict visual performance"; Journal of Vision; Apr. 23, 2004; vol. 4(4); pp. 322-328.
Navarro et al.; Accommodation-dependent model of the human eye with aspherics; J. Opt. Soc Am. A; vol. 2; No. 8; Aug. 1985; pp. 1273-1281.
Watsky, M.A. et al., "Predicting Refractive Alterations with Hydrogel Keratophakia," Investigative Opthalmology & Visual Science, vol. 26, pp. 240-243, Feb. 1985.
Jankov et al.; Laser intrastromal keratoplasty—case report; J. Refract.Surg.; 20(1); pp. 79-84; Jan.-Feb. 2004.
Sharma; U.S. Appl. No. 14/427,510 entitled "Corneal implant edges and methods of use," filed Mar. 11, 2015.
Holliday et al.; U.S. Appl. No. 14/656,621 entitled "Methods of correcting vision," filed Mar. 12, 2015.
Esguerra et al.; U.S. Appl. No. 14/688,226 entitled "Corneal implant delivery devices and methods of use," filed Apr. 16, 2015.
Sharma et al.; U.S. Appl. No. 14/211,714 entitled "Pre-treatment haze reduction for corneal inlays," filed Mar. 14, 2014.
Long et al.; U.S. Appl. No. 14/217,056 entitled "Anterior corneal shapes and methods of providing the shapes," filed Mar. 17, 2014.
Winn et al.; Factors affecting light-adapted pupil size in normal human subjects; Investigative Ophthalmology and Visual Science; 35(3); pp. 1132-1137; Mar. 1994.
Collins et al.; U.S. Appl. No. 14/575,833 entitled "Integrated part fixturing for lathing processes," filed Dec. 18, 2014.
Dymax; UV curable optical assembly; 2 pages; retrieved Mar. 4, 2015 from the internet (http:www.dymax.com/index.php/adhesives/optical).
Walker et al.; Clinical Methods: The history, physical, and laboratory examinations; 3rd Edition; Chapter 58; Butterworth Publishers; Jul. 1990; 8 pages; retrieved from the internet (http://www.ncbi.nlm.nih.gov/books/NBK381).
Plambeck et al.; U.S. Appl. No. 15/163,610 entitled "Corneal implant storage and delivery devices," filed May 24, 2016.
Holliday; U.S. Appl. No. 15/313,297 entitled "Corneal implants and methods of manufacturing," filed Nov. 22, 2016.
Spector; Chapter 58: The Pupils; in Clinical Methods: The history, physical, and laboratory examinations; Butterworth Publishers; 3rd Edition; 8 pgs; retrieved from the internet (https://www.ncbi.nlm.nih.gov/books/NBK381/); published Jul. 1990.
Le et al.; U.S. Appl. No. 15/508,499 entitled "Training cornea for refractive surgery training," filed Mar. 3, 2017.

* cited by examiner

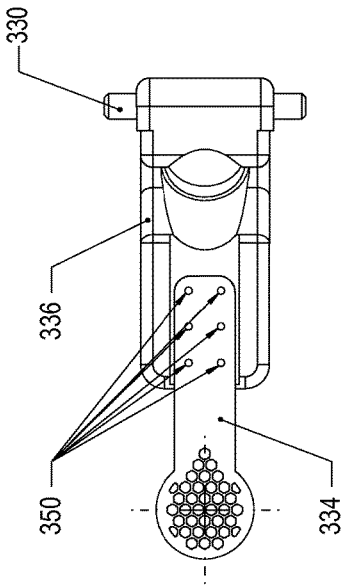
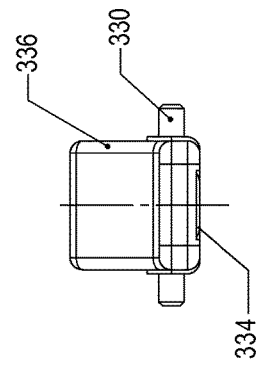
FIG. 23C
FIG. 23D
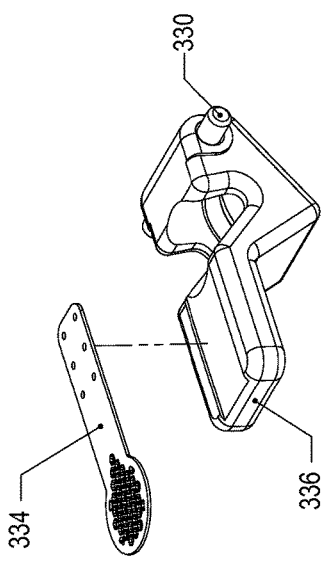
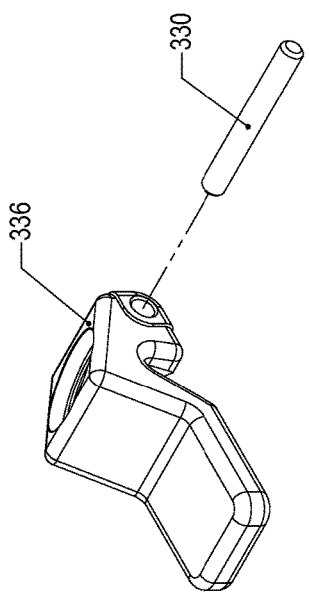
FIG. 23A
FIG. 23B

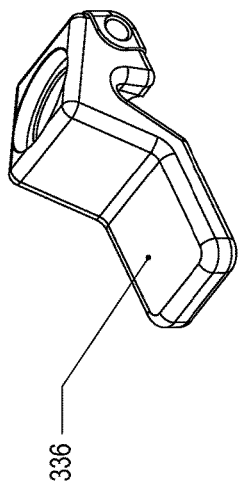
FIG. 24F
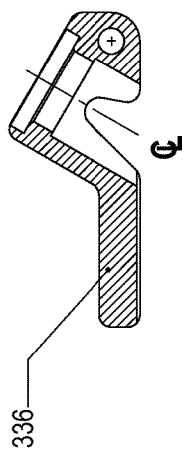
SECTION A-A
FIG. 24D
FIG. 24C
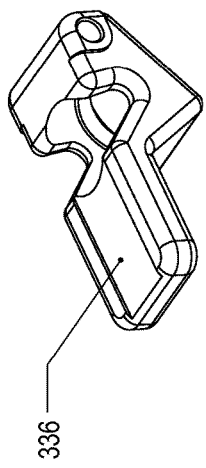
FIG. 24E
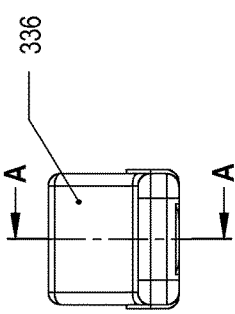
FIG. 24A
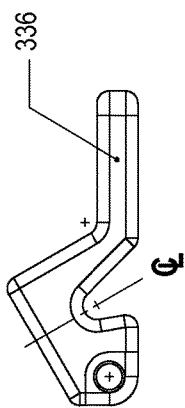
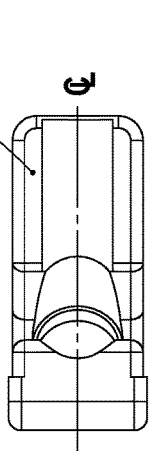
FIG. 24B

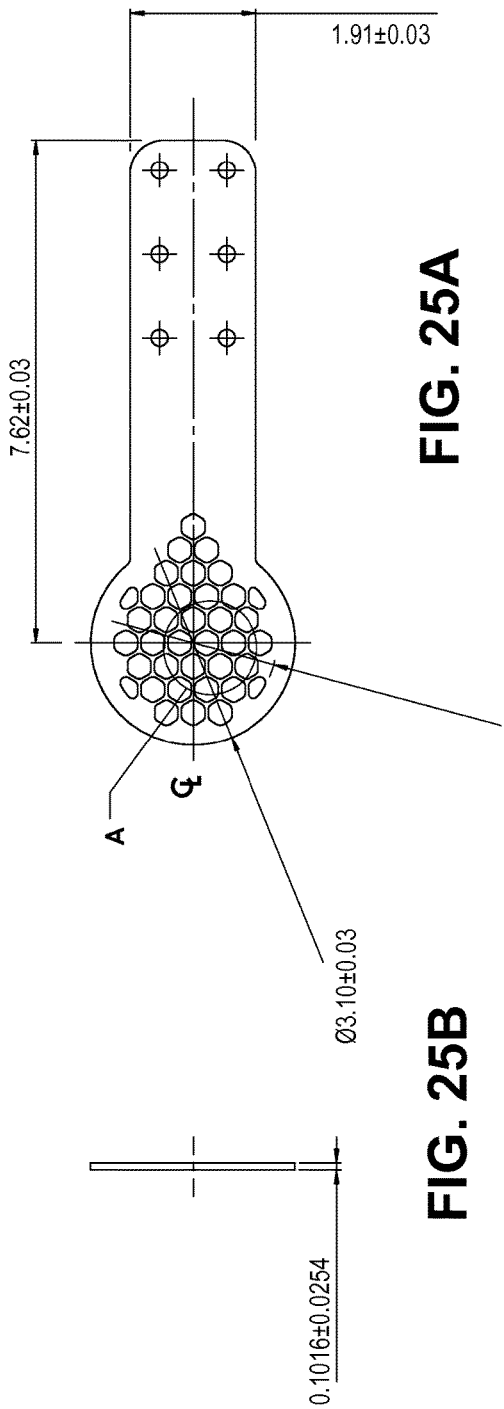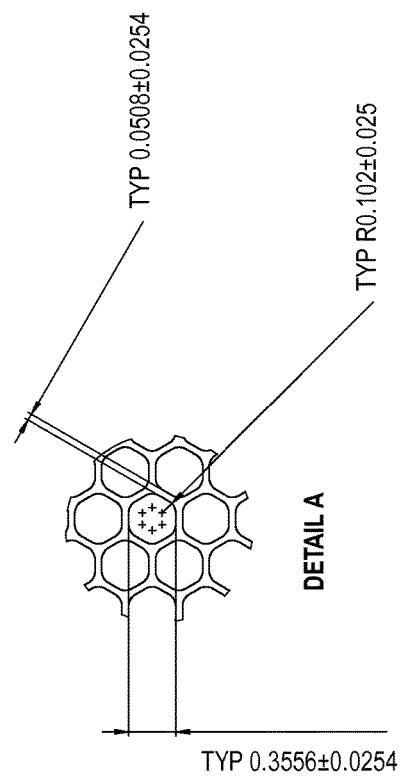
FIG. 25A
FIG. 25B
FIG. 25C

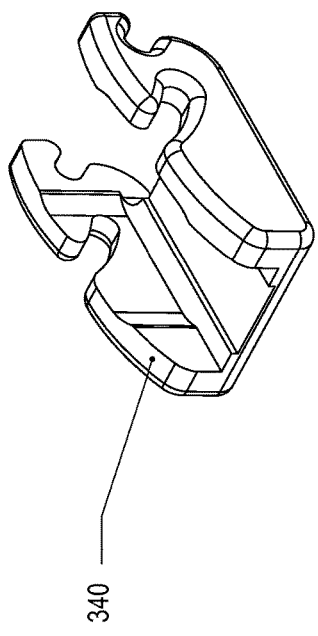
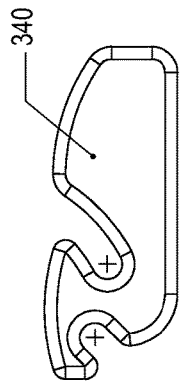
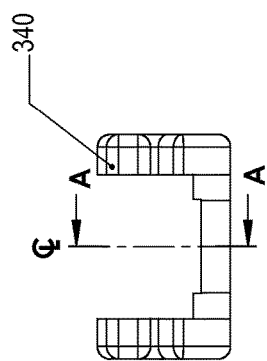
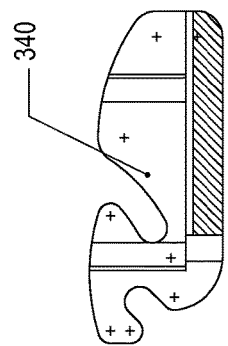
FIG. 27E
FIG. 27C
FIG. 27A
FIG. 27B
SECTION A-A

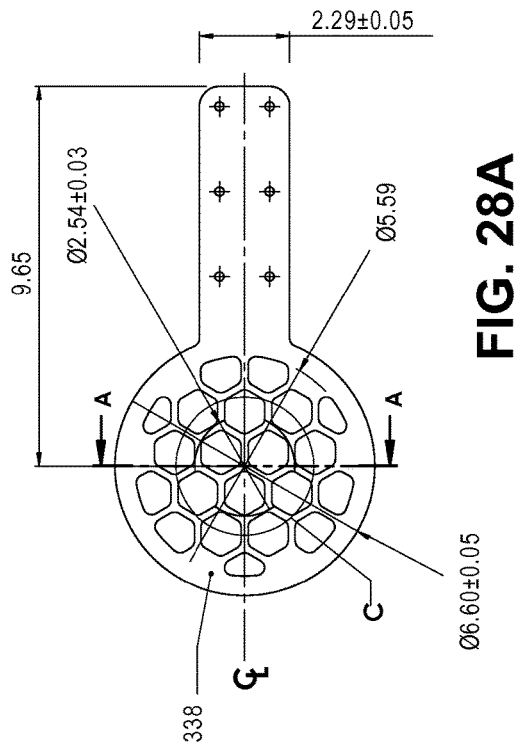
FIG. 28A
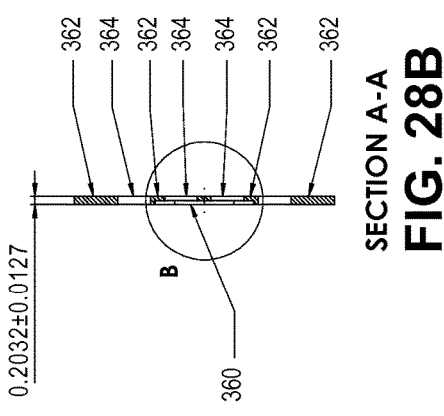
SECTION A-A  FIG. 28B
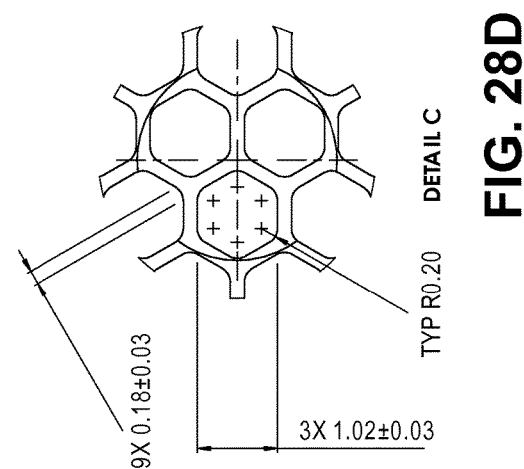
FIG. 28C
FIG. 28D

SECTION A-A

SECTION A-A

SCALE 1:2

SECTION A-A
SCALE 2:1

FIG. 33B SECTION B-B

FIG. 33C SECTION A-A

FIG. 33D DETAIL C

CORNEAL IMPLANT APPLICATORS

CROSS REFERENCE TO RELATED APPLICATIONS

This application is a continuation of U.S. application Ser. No. 13/657,650, filed Oct. 22, 2012, now U.S. Pat. No. 8,668,735, which application is a continuation-in-part of U.S. application Ser. No. 13/443,696, filed Apr. 10, 2012, now U.S. Pat. No. 9,005,280, which is a continuation of U.S. application Ser. No. 13/206,200, filed Aug. 9, 2011, now abandoned, which is a continuation of U.S. application Ser. No. 11/422,815, filed Jun. 7, 2006, now U.S. Pat. No. 7,992,906, which is a continuation of U.S. application Ser. No. 11/054,639, filed Feb. 9, 2005, now U.S. Pat. No. 7,128,351, which is a continuation of U.S. application Ser. No. 10/463,091, filed Jun. 17, 2003, now U.S. Pat. No. 6,893,461, which is a division of U.S. application Ser. No. 09/843,547 filed Apr. 26, 2001, now U.S. Pat. No. 6,581,993, which is a continuation-in-part of U.S. application Ser. No. 09/660,371, filed Sep. 12, 2000, now U.S. Pat. No. 6,543,610; all disclosures of which are incorporated herein by reference.

U.S. application Ser. No. 13/657,650, filed Oct. 22, 2012, also claims priority to the following provisional applications: U.S. 61/550,185, filed Oct. 21, 2011; U.S. 61/679,482, filed Aug. 3, 2012; and U.S. 61/606,674, filed Mar. 5, 2012; all disclosures of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Corneal implants, such as corneal onlays and corneal inlays, can be small, delicate medical devices, the storage and/or handling of which should be carefully performed to prevent damage to the implants. Additionally, corneal implants can also be transparent, which, in addition to their small size, can make them difficult to see with the unaided eye.

Devices and methods are needed that allow for easy handling and positioning of small, delicate corneal implants without damaging the implant.

SUMMARY OF THE DISCLOSURE

One aspect of the disclosure is a corneal implant applicator apparatus, comprising a corneal applicator member comprising an applicator; a corneal implant support disposed relative to the applicator to form an implant chamber; and wherein the applicator and the corneal implant support are adapted such that a corneal implant has a greater preference for adhering to the applicator than to the corneal implant support.

In some embodiments the applicator is adapted such that the corneal implant has a greater preference for adhering to corneal tissue than to the applicator. The applicator can have a radius of curvature that is greater than a radius of curvature of an anterior surface of the corneal implant.

In some embodiments the applicator has at least one opening therethrough. The corneal implant support can also have at least one opening therethrough.

In some embodiments the corneal implant support has a surface with a contour different than a contour of a surface of the applicator, and wherein the different contours provide the corneal implant with the greater preference for adhering to the applicator than to the corneal implant support. The applicator surface can be smoother than the surface of the corneal implant support.

In some embodiments the corneal implant support is adapted to be moved relative to the applicator to provide access to the corneal implant and allow the corneal implant to preferentially adhere to the applicator. The corneal implant support can be detachably secured to the applicator. The apparatus can further comprise at least one clip adapted to detachably secure the corneal implant support to the applicator.

In some embodiments the apparatus further comprises a fluid disposed within the implant chamber.

In some embodiments the corneal implant is made from a hydrophilic, such as a hydrogel, material.

In some embodiments the applicator and corneal implant support are adapted such that the net adhesive forces between the applicator and the corneal implant are greater than the net adhesive forces between the implant support and the corneal implant, whereby the corneal implant will preferentially adhere to the applicator when the applicator and corneal implant support are moved relative to one another.

One aspect of the disclosure is a method of depositing a corneal implant onto corneal tissue, comprising providing a corneal implant applicator apparatus, the apparatus comprising a corneal implant applicator, an implant support disposed relative to the corneal implant applicator to form an implant chamber, and a corneal implant disposed in the implant chamber, moving the implant support relative to the corneal implant applicator to provide access to the corneal implant and to allow the corneal implant to preferentially adhere to the corneal implant applicator rather than the implant support, positioning the corneal implant applicator such that the corneal implant engages corneal tissue, and moving the corneal implant applicator from the corneal tissue to allow the corneal implant to preferentially adhere to the corneal tissue rather than the applicator, thereby depositing the corneal implant on the corneal tissue.

In some embodiment moving the implant support relative to the corneal implant applicator comprises removing a securing element that detachably secures the implant support to the corneal implant applicator.

In some embodiments the method further comprises wicking away fluid from within the implant chamber, wherein the wicking step occurs prior to moving the implant support relative to the corneal implant applicator.

In some embodiments the method further comprises, prior to the depositing step, creating a corneal flap and lifting the corneal flap to expose the corneal tissue.

BRIEF DESCRIPTION OF THE DRAWINGS

FIGS. 19-22 illustrate an exemplary corneal implant applicator apparatus.

FIGS. 23A-35B illustrate components of an exemplary corneal implant applicator apparatus.

DETAILED DESCRIPTION

The disclosure relates to devices for one or more of packaging, storing, positioning, and delivering corneal implants such as corneal inlays. The devices herein can be used in the movement and positioning of, for example without limitation, corneal onlays, corneal inlays, corneal replacements, and contact lenses.

Figure 1A:
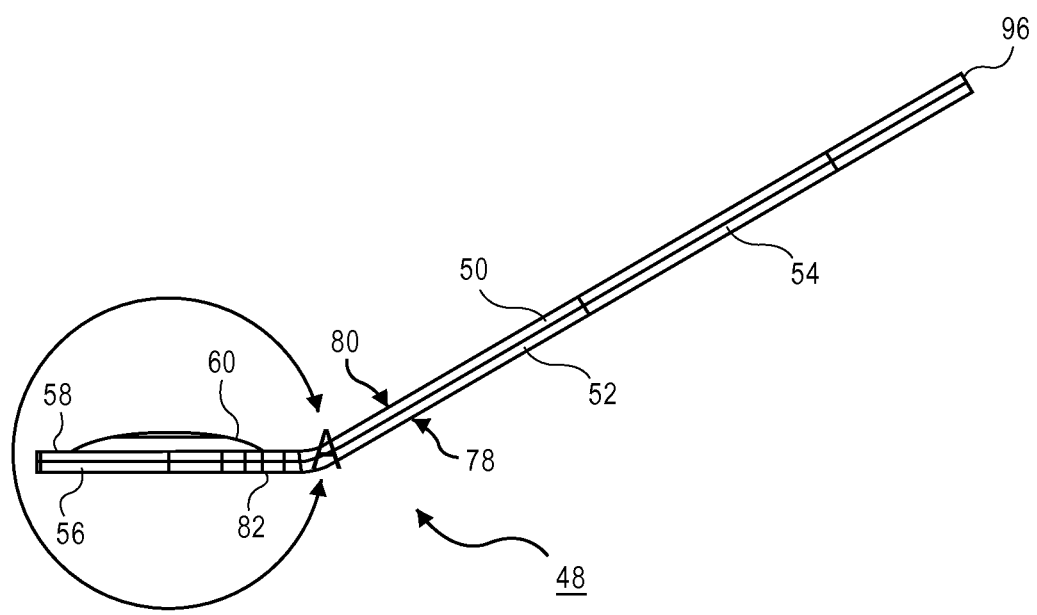
FIGS. 1a-3c illustrate an exemplary corneal implant applicator apparatus.

FIGS. 1A-3C illustrate an exemplary embodiment of an implant packaging and handling system 48 adapted to apply a corneal implant to a corneal surface. Referring to FIG. 1A, system 48 includes implant carrier member 80 having a handle 50 extending from implant applicator 58. Implant carrier member 80 is adapted to detachably couple to implant support member 78. As illustrated, implant support member 78 has a handle 52 extending from implant support 56.

Figure 1B:
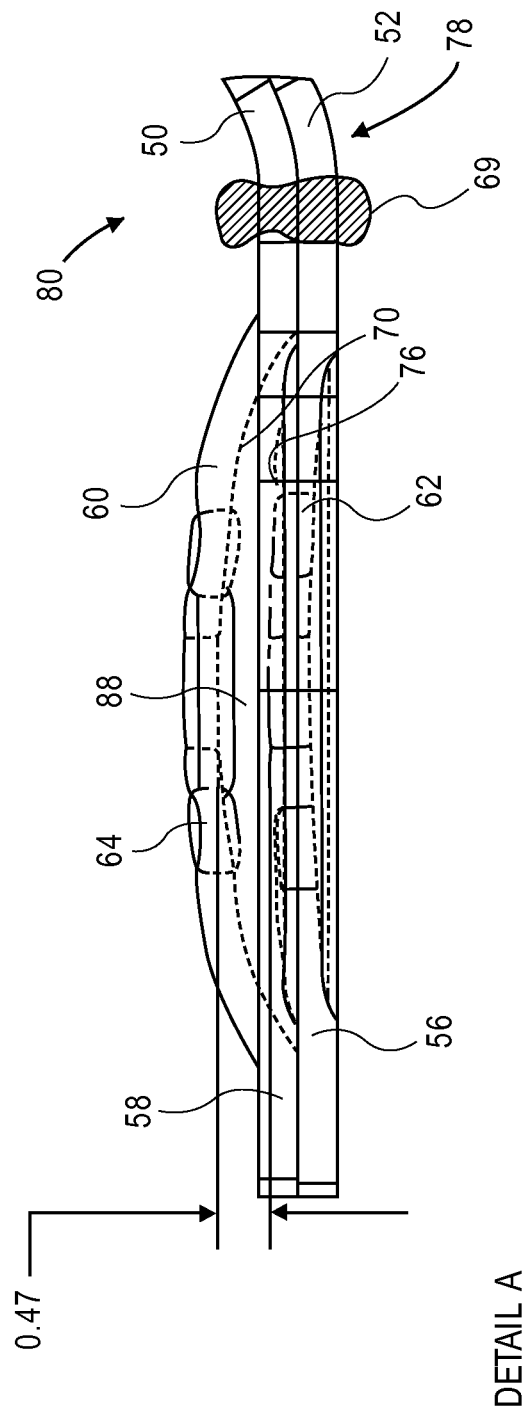

FIG. 1B illustrates detail "A" shown in FIG. 1A. As illustrated in FIG. 1B, fastening carrier member 80 and support member 78 together operably aligns implant applicator 58 and implant support 56. In this embodiment, the handle portions 50 and 52 are positioned adjacent to one another so as to form a support handle 54 (see FIG. 1A). Concave surface 70 of applicator 58 is aligned with convex implant support surface 76 of implant support 56. Surface 70 and surface 76 form chamber 88 therebetween, which provides a storage space to retain a corneal implant therein.

Figure 2A:
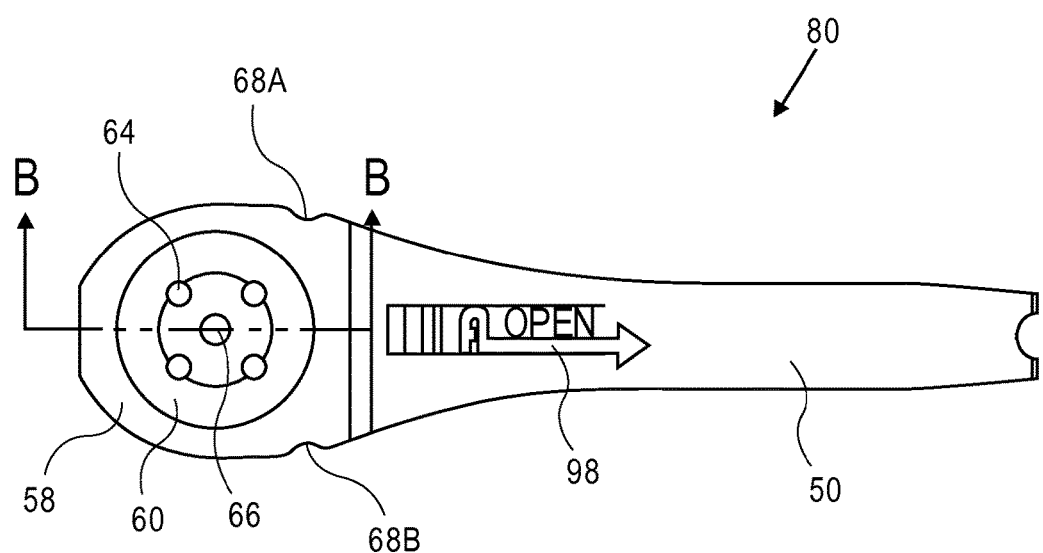
Figure 2B:
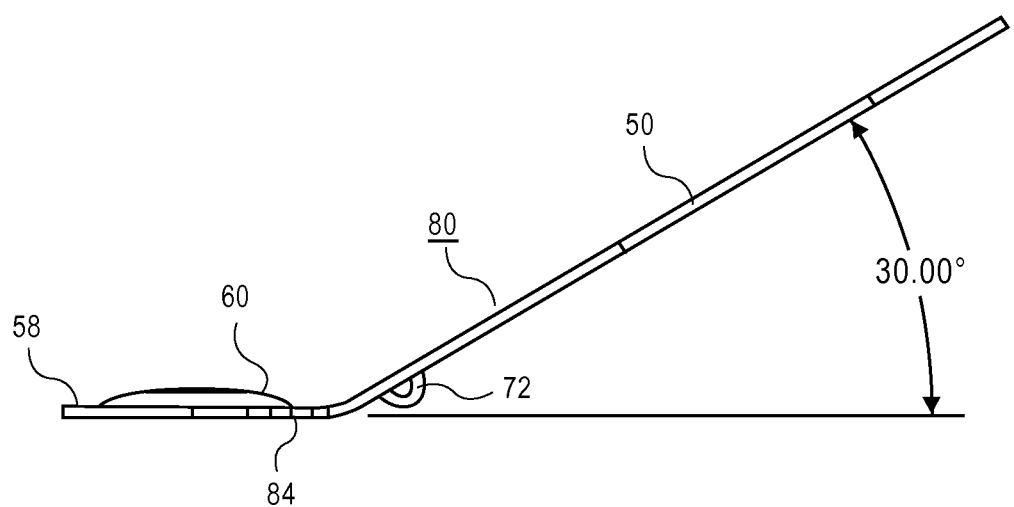
Figure 2C:
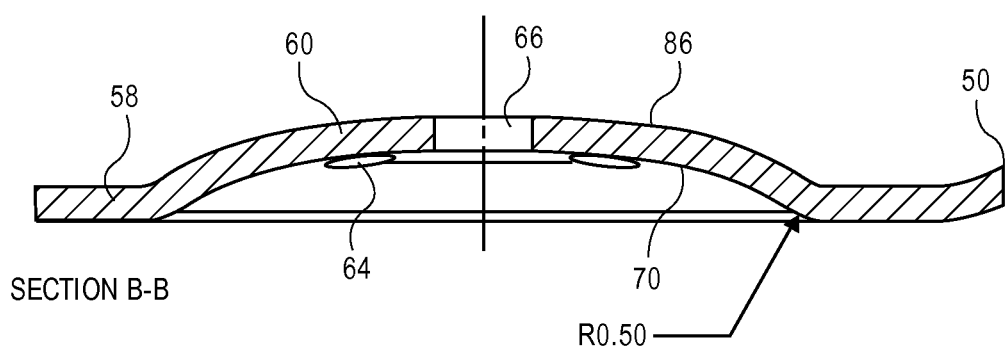

FIGS. 2A-2C illustrate views of carrier member 80 (support member 78 not shown for clarity). FIG. 2A illustrates a top view of a portion of carrier member 80, showing handle 50 and implant applicator 58. FIG. 2C shows detail "B" from FIG. 2A. In FIG. 2C, applicator 58 includes a domed portion with upper surface 86 and lower surface 70. Lower surface 70 is contoured with a radius of curvature that is greater than the radius of curvature of an anterior surface of the implant that is being packaged (not shown for clarity). The difference in the radii of curvature is advantageous in assisting with the release of the corneal implant from applicator surface 70. More particularly, a corneal implant generally includes a posterior surface that is adapted to make contact with corneal bed tissue, and an anterior surface that faces in the anterior direction and is disposed under overlying corneal tissue (whether the implant is inserted under a flap or into a pocket).

In use, applicator surface 70 (on which an implant is retained) is first positioned immediately over the corneal bed surface such that the implant engages the corneal bed tissue. Applicator 58 (and therefore surface 70) is then lifted away from the corneal bed surface. The anterior surface of the implant releases from applicator surface 70 and the posterior surface of the implant remains adhered to the corneal bed surface. To enhance deposition of the implant onto the corneal bed surface and prevent the implant from remaining adhered to applicator surface 70, applicator surface 70 has a radius of curvature that is greater than the radius of curvature of the anterior surface of the implant. Due to the difference in radii of curvature, the anterior surface of the implant and applicator surface 70 are not complementary, and thus, are more easily separated. In this manner the corneal implant preferentially adheres to the cornea over applicator surface 70.

Figure 12:
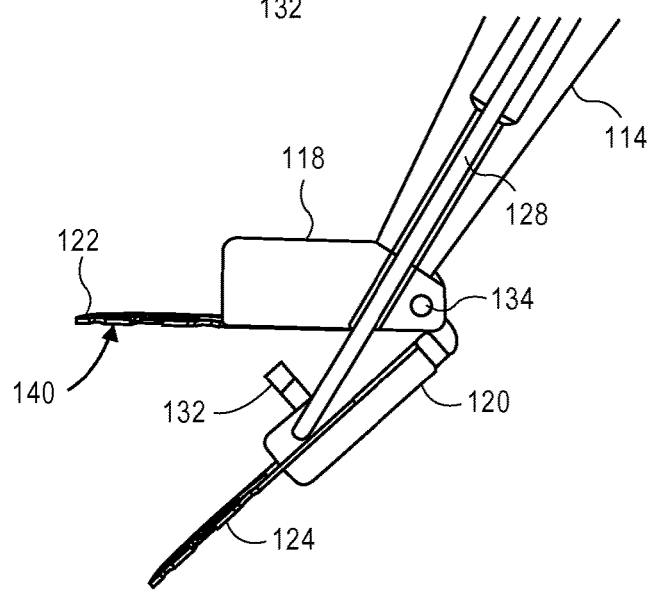

In other embodiments applicator surface 70 has an indented ring or recessed applicator surface (as is shown in FIG. 12 and indicated by numeral 29 in U.S. Pat. No. 6,581,993, incorporated by reference herein). The recessed surface can be circular, thereby allowing a substantially circular implant to be centrally positioned on applicator surface 70.

To further enhance disassociation of the corneal implant from applicator surface 70, a plurality of openings 64 are provided through applicator surface 70 through which a volume of fluid can be passed to help remove the implant. Alternatively, fluid can be withdrawn through the opening 64 from the implant that is disposed on applicator surface 70. Particularly, the openings 64 provide a fluid passage for drawing fluid away from the implant using a cotton swab, or other absorbent material, that would be positioned against upper surface 86 of applicator 58. Additionally, optional central opening 66 is provided in applicator 58 to assist with the proper alignment of the implant and the deposition of the implant onto the cornea surface. Specifically, a cannula or like instrument can be inserted through central opening 66 to depress and assist the release of the implant from applicator surface 70. The diameter of central opening 66 is greater than the diameter of openings 64. In this way, the user is provided with a central point of reference, which enables the user to align applicator surface 70 with the optical axis of the eye, and, thus, properly position the implant.

Figure 3A:
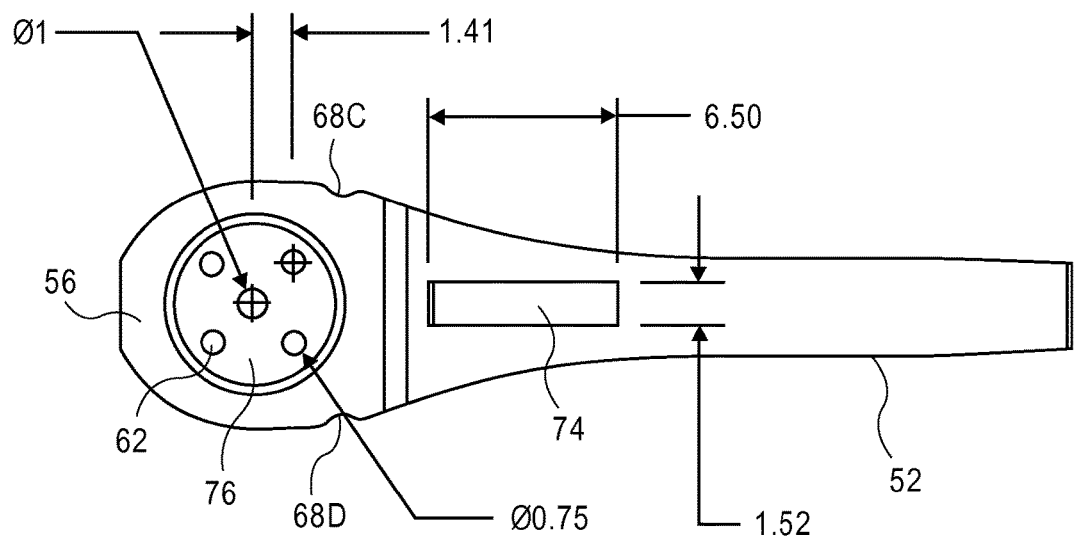
Figure 3B:
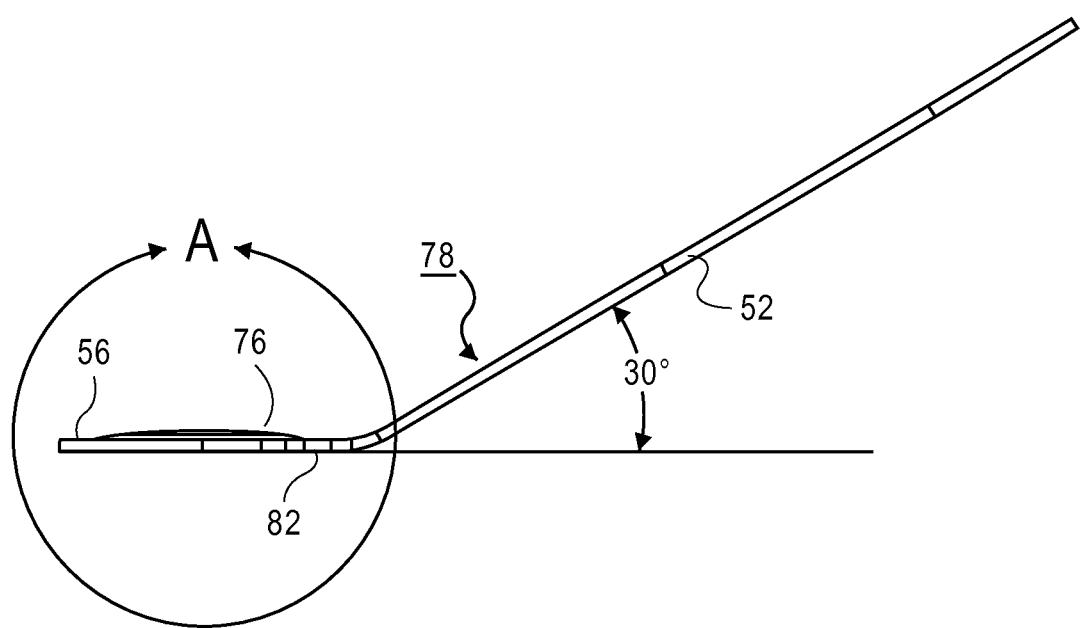
Figure 3C:
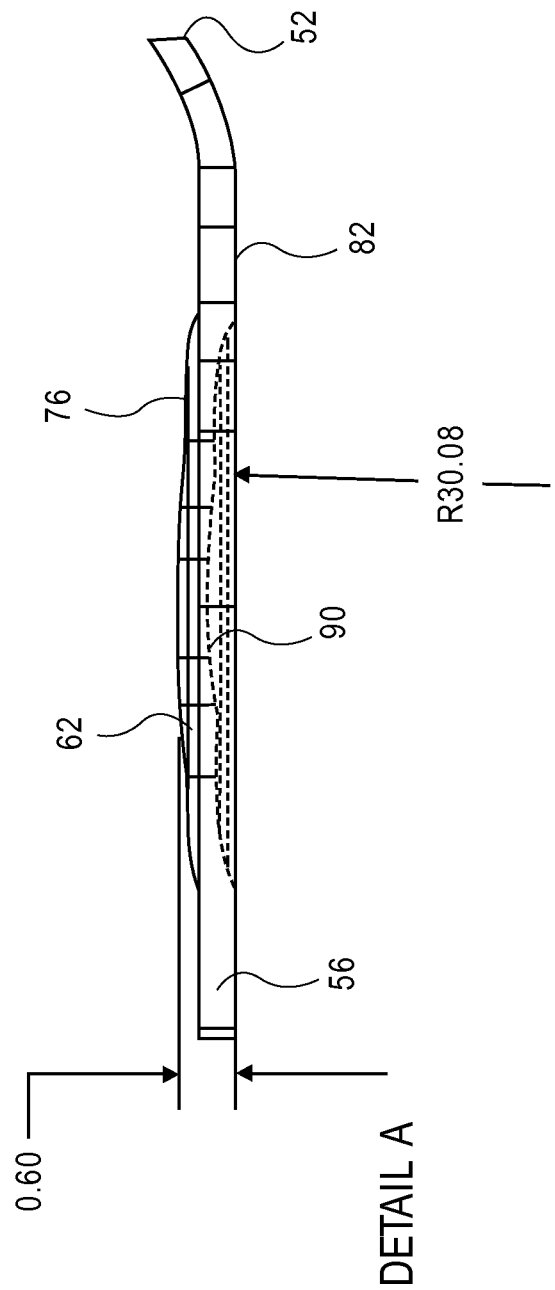

FIGS. 3A-3C illustrate different views of support member 78 (carrier member not shown for clarity). FIG. 3C illustrates detail "A" from FIG. 3B. Support member 78 has handle 52 extending from implant support 56. Implant support 56 comprises platform 82 disposed about an upper support surface 76 and an opposing lower surface 90. Lower surface 90 is recessed relative to the lower surface of the platform portion 82. Upper surface 76 and lower surface 90 have a plurality of openings therethrough to facilitate the passage of liquid to and away from the implant.

As shown in FIG. 3B, support 56 is shown at an angle of 30° relative to handle 52. It can be advantageous for support 56 to be at an angle relative to handle 52 between about 30° and about 60°. Similarly, the angle between applicator 58 and handle 50 is generally between about 30° and about 60°. In FIG. 2B the angle is 30°. In some embodiments the angle between handle portions 50 and 52 and platform portions 84 and 82, respectively, is about 45°. It is to be understood that a range of angles can be used without deviating from the scope of the present disclosure.

FIGS. 1B, 2A, and 3A illustrate an exemplary embodiment in which support member 78 is detachably connected to carrier member 80. Specifically, as illustrated by FIG. 2A, the carrier member 80 is provided with a pair of notches or grooves, 68a and 68b. Notches or grooves 68a and 68b are located on opposite sides of applicator 58. Likewise, support member 78 is provided with a pair of notches or grooves, 68c and 68d, located on opposite sides of implant support 56. Carrier member 80 can be securely coupled to support member 78 by aligning notch 68a with 68c, and notch 68b with 68d, and then positioning a fastening element about the two members and securely within the aligned notches. FIG. 1B shows elastic band 69, which is placed about members 78 and 80, secured within each of the respective notches (68a-d) to secure members 78 and 80 together in a detachable manner. In alternative embodiments metal or plastic clips are used to fasten together members 78 and 80. It should be understood, however, that various ways can be utilized to fasten the two members together in a detachable manner without deviating from the scope of the disclosure.

FIGS. 2B and 3A illustrate an additional optional way to secure members 78 and 80 together and such that they can be easily separated to prepare the implant for use. Handle 52 includes slot 74 adapted to receive and interlock with tab 72 of carrier member 80. Tab 72 extends from the lower surface of handle 50 of carrier member 80. In use, carrier member 80 is positioned in overlapping relation to support member 78 such that tab 72 is inserted into slot 74. Once inserted, tab 72 holds carrier member 80 together with support member 78. To provide additional attachment, band 69 is then placed about implant applicator 58 and implant support 56, as is described in more detail above. In use, the user initially removes band 69 or other attachment element from the fastened members 78 and 80. Once removed, the user simply slides handle 50 in the direction indicated by arrow 98 shown in FIG. 2A, which is generally a proximal direction. In this way, tab 72 slidably disengages from slot 74 and members 78 and 80 are separated. Once separated, carrier member 80 can then be used to deposit the implant onto the cornea surface as set forth above. The proximal portion of handle 50 is also adapted to be secured to a surgical-style handle or other handle device to more easily deposit the implant onto the corneal bed surface.

Support surface 76 of implant support 56 is adapted such that the implant will preferably remain adhered to applicator surface 70 upon separation of members 78 and 80. In this embodiment support surface 76 has a more uneven or rough contour than adjacent applicator surface 70. Applicator surface 70 is provided as a smooth or polished surface. In this embodiment, it is not critical that surface 70 be microscopically smooth, though it may be. In this embodiment, however, it is important that surface 70 be smoother than support surface 76. In this manner, applicator surface 70 has a smoother surface area for directly contacting and adhering to the lens implant.

Support surface 76 is fabricated so as to have a contour characterized by minute bumps or rounded portions along surface 76. In some embodiments this contoured surface can be fabricated by manufacturing support surface 76 from polypropylene comprising polytetrafluoroethylene beads embedded in the polypropylene surface. Polytetrafluoroethylene is sold under the trade name TEFLON. In this embodiment, the beads maintain their general conformation when embedded, which results in surface 76 having raised bumps, rounded portions, or the like. Alternatively, support surface 76 can be roughened, etched, notched, scored or made to be imperfect using any one of molding, stamping or other known mechanical techniques. Surface 76 is less able to adhere to the surface of the implant than is smoother applicator surface 70, and the implant will preferentially remain adhered to applicator surface 70 upon separation of the members 78 and 80.

Additionally, the implant can be further directed to remain adhered on applicator surface 70. For example, system 48 can be removed from a storage container in which system is disposed (not shown). System 48 is turned such that carrier member 80 is facing downwards and support member 78 is on top. Next, the user simply places an absorbent material against the top surface 60 of applicator portion 58 so as to draw fluid from within chamber 88 through openings 64. As the fluid is drawn away from chamber 88 the implant is lowered to a resting position against the applicator surface 70.

One or more of the various components of system 48 can be made from a polymer or plastic material. For example, system 48 components could be made from one or a combination of the following polymers: Polytetrafluoroethylene (sold under the trade name TEFLON), Polypropylene, or Polysulfone (sold under the trade name UDEL). Alternatively, portions of each component member could be made from a polymer or plastic together with a portion comprising stainless steel or other metal or semi-metal. For instance, handle 50 of carrier member 80 can be manufactured from stainless steel, and applicator portion 58 can be manufactured from a polymer material. The handle and applicators could then be welded or interlocked together using various known fabrication techniques. It should also be understood that various other polymers or polymer combinations can be utilized without deviating from the scope of the present invention.

System 48 is adapted to maintain the corneal implant in a hydrated condition during storage and shipping. System 48 can be positioned within a storage device such as a vial as is described in U.S. Pat. No. 6,543,610, incorporated by reference herein. When system 48 is placed in a storage device with fluid therein, the corneal implant is in contact with a volume of storage fluid. In this way, the implant is contained within the chamber 88 and maintained in a hydrated condition by the passage of fluid through the respective openings 62, 64, and 66.

The corneal implant is packaged within chamber 88 defined by applicator surface 70 and carrier support surface 76. The height of this space is designed to be sufficiently narrow that the implant remains properly oriented within chamber 88 during storage and handling conditions. In this way, the user simply detaches carrier member 80 from support member 78 and deposits the implant to the corneal surface by placing the applicator surface 70, on which the implant is adhered, directly to the corneal surface.

The disclosure below describes devices and methods of use that rely at least partially on surface tension of liquids to control the positioning and/or movement of a corneal implant. The devices can be used in the storage, packaging, movement, or delivering of the corneal implants. These approaches can be used when the corneal implant is made at least partially of hydrophilic material, such as a hydrogel.

Figure 4:
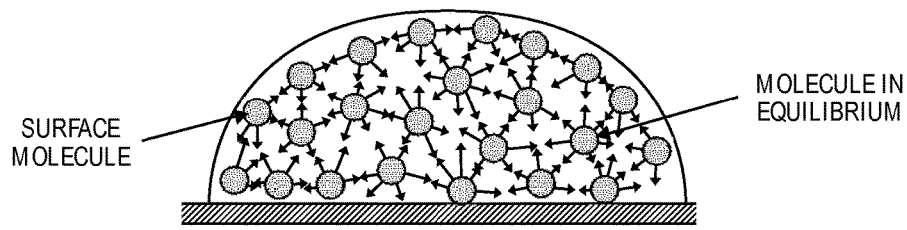
FIG. 4 illustrates exemplary cohesive forces.

Surface tension is the property of liquids that allows the surface of a body of liquid to resist external forces. It is what allows objects denser then water, such as small pins and certain insects, to float on a liquid's surface. Surface tension is caused by the cohesive forces of a liquid's molecules. Cohesive forces are the attractive forces between two like molecules. As shown in FIG. 4, an average molecule within a body of liquid has no overall cohesive force acting upon it because it sees cohesive forces from neighboring molecules acting upon it in every direction. A molecule on the surface, however, only sees cohesive forces pulling it inwards. For very small droplets, the inward force on all surface molecules causes the droplet to be generally spherical in shape.

Figure 5:
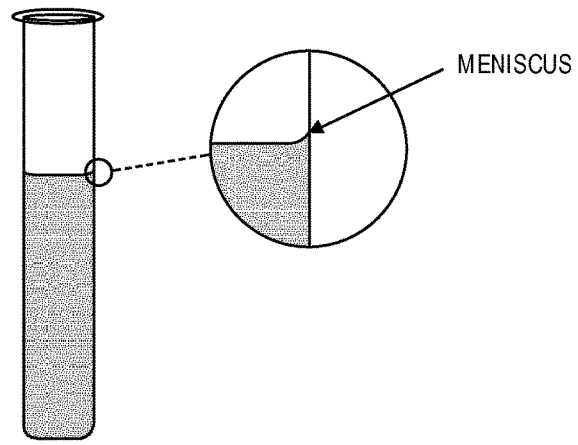
FIG. 5 illustrates exemplary adhesive forces.

Adhesive forces, on the other hand, are those seen between unlike molecules. For some material combinations, these forces can be greater than the cohesive forces of a liquid's molecules. These strong adhesive forces are the cause of an upward 'bowing,' called the meniscus (as shown in FIG. 5), in a liquid's surface where the liquid around the edge of a container is pulled higher than the rest of the surface by the adhesive forces between the liquid and the container. The adhesive forces pull up on the surface of the water and are in equilibrium with the gravitational forces pulling down on the body of liquid.

Figure 6:
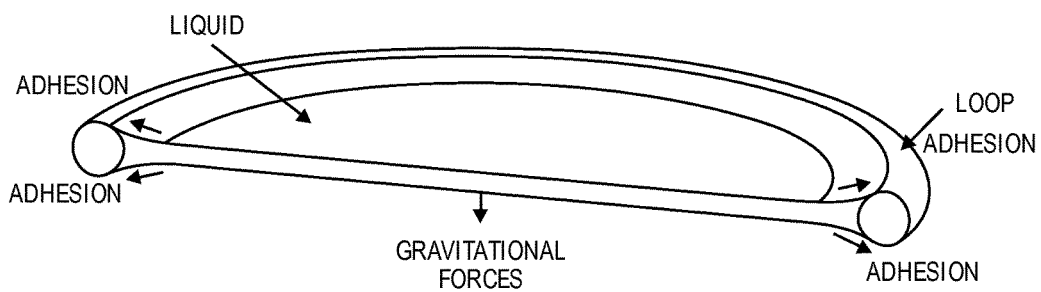
FIG. 6 illustrates a liquid suspended within a loop

In the case of liquid suspended within a loop, as shown in FIG. 6, adhesion forces from the loop act on both the top and bottom surfaces of the liquid and cohesive forces act across both upper and lower surfaces. These forces are sufficient to hold a liquid within a loop up until the liquid's volume is so great that the gravitational forces overcome the cohesive and adhesive forces.

In the case of a solid, mesh, or other such surface, the adhesive and cohesive forces act in a similar fashion. Many factors, including the type of material, the type of fluid, and the surface geometry will affect the strength of the adhesive and cohesive forces.

Exemplary corneal implants that can be stored and used in the following embodiments are corneal inlays described in U.S. Pub. No. US 2007/0203577, filed Oct. 30, 2006, now U.S. Pat. No. 8,057,541, U.S. Pub. No. US 2008/0262610, filed Apr. 20, 2007, and U.S. Pub. No. 2011/0218623, filed Sep. 8, 2010, the disclosures of which are incorporated herein by reference. In some embodiments, a "small diameter" (i.e., between about 1 mm and about 3 mm) corneal inlay is made from a hydrogel, that may be primarily fluid. This, as well as the inlay's small size, causes it to behave in somewhat the same way as a fluid. The disclosure below makes use of these characteristics of the corneal implant and the adhesion forces between a fluid and various surface geometries. While the disclosure herein focuses on corneal inlays, any corneal implant that exhibits similar properties can be used as described herein. For example, corneal onlays, at least a portion of which have hydrophilic properties, can be used as described herein.

The devices herein rely on a body's "affinity" for a fluid or an object with fluid-like properties (e.g., a hydrophilic corneal implant). As used herein, a body's "affinity" for the fluid or fluid-like object is influenced by the difference between the strength of the net adhesive forces between the body and the fluid or fluid-like object and the strength of the net cohesive forces within the fluid or fluid-like object. In embodiments herein where there is a substantially constant fluid or fluid-like object (e.g., a hydrophilic corneal inlay), the relative affinities of two bodies for the fluid or fluid-like object is at least partially determined by the relative strengths of the net adhesive forces between the bodies and the fluid or fluid-like object. For example, in an embodiment in which the fluid-like object is a hydrophilic corneal implant, a first body can have a greater affinity for the implant than a second body when the net adhesive forces between the first body and the implant are greater than the net adhesive forces between the second body and the implant.

The corneal implant will remain adhered to the body with the highest net force (the sum of the adhesive and cohesive forces).

A first body, referred to herein as a "moderate body," has a greater affinity for the fluid or fluid-like object than a second body, referred to herein as a "minimal body." As used herein in this context, "body" may be used interchangeably with device, component, structure, or other similar term to indicate anything with structure. The eye, however, has a greater affinity for the fluid or fluid-like object than the moderate body. The different relative affinities can be used to handle the inlay and control the movement of the inlay as it is moved from one surface to another without a user needing to touch it with a hand or other tool. Factors that influence the relative affinities include one or more of: the type of material, the type of fluid, and the surface geometry including surface area.

As used herein, a corneal inlay (e.g., the fluid-like object) has a greater "affinity" for the corneal bed of the eye than it does the moderate body, and at the same time the inlay has a greater affinity for the moderate body than it does the minimal body. The eye can be described as having a greater affinity for the inlay than both the moderate body and the minimal body. Similarly, the moderate body can be described as having a greater affinity for the inlay than the minimal body. That is, the affinity between two bodies can be described relative to either body. That is, for example, the moderate body has a greater affinity for the inlay than does the minimal body, and thus the inlay will preferentially adhere to the moderate body over the minimal body.

In some embodiments the storage fluid is water or saline, for example. Water molecules are highly polarized, which provides for attractive forces with other materials.

A relative comparison of the affinity between each body and the inlay can be represented by: corneal tissue>moderate body>minimal body. The moderate and minimal bodies may take on many forms, including, without limitation, meshes, membranes, and/or material with different surface finishes or contours.

Due to the differences in affinity between the minimal body and the moderate body, the inlay preferentially remains adhered to the moderate body. It continues to adhere to the moderate body until exposed to a stronger adhesive force. The minimal and moderate bodies can therefore be any suitable material as long as the adhesive forces between the moderate body and the inlay are greater than the adhesive forces between the minimal body and the inlay. The moderate body has a greater affinity for the inlay than does the minimal body, and the adhesive properties of the materials is a factor influencing those affinities.

Figure 7:
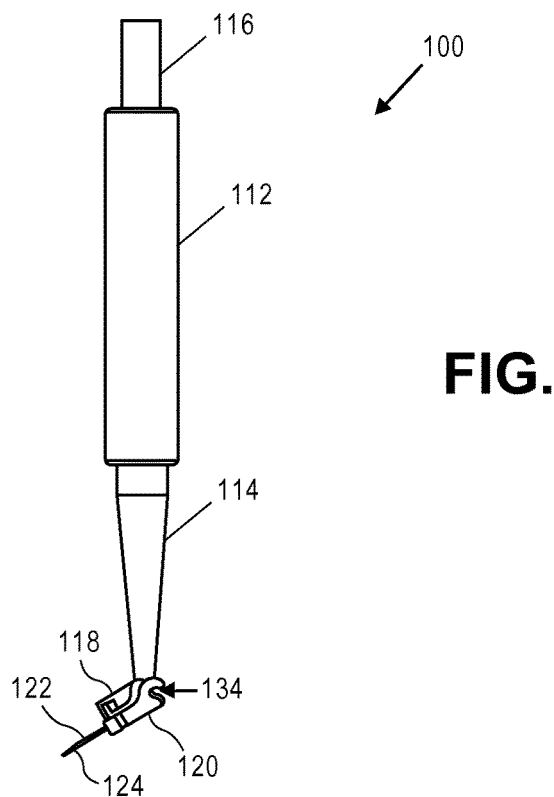
FIGS. 7-13 illustrate an exemplary corneal implant applicator apparatus.
Figure 8:
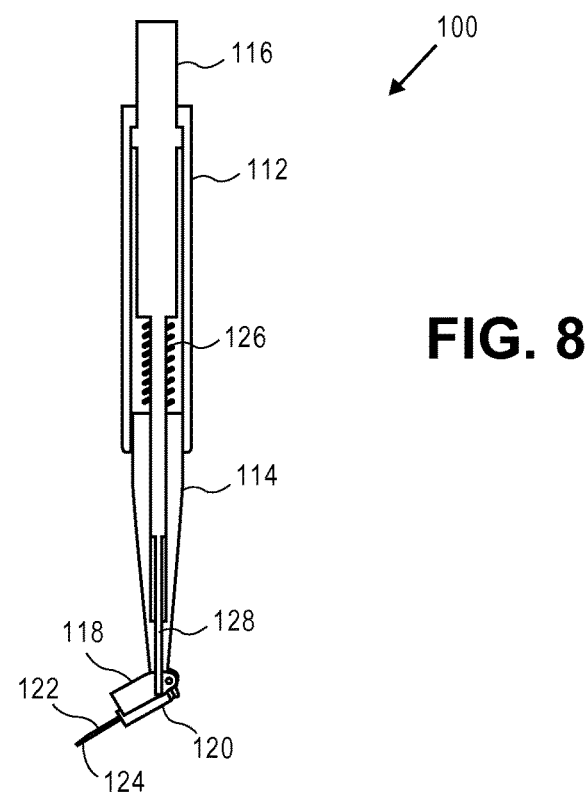

FIGS. 7-14D illustrate an exemplary embodiment of an apparatus that comprises a moderate body and a minimal body, wherein the apparatus also includes an actuation mechanism that is used to separate the minimal body from the corneal implant and the moderate body. The apparatus can be used to store the corneal implant, prepare the corneal implant for delivery, and/or deliver the corneal implant onto or into the eye. FIGS. 7 and 8 (side view and sectional side view, respectively) illustrate device 100 including handle 112 secured to distal portion 114. Actuator 116 is disposed in both handle 112 and distal portion 114, both of which are adapted to allow actuator 116 to pass therethrough. Spring 126 maintains actuator 116 in the at-rest, or non-actuated, configuration shown in FIGS. 7 and 8. Actuator 116 has a distal section 128 with a reduced size that is disposed in a smaller sized distal channel in distal portion 114.

Figure 9:
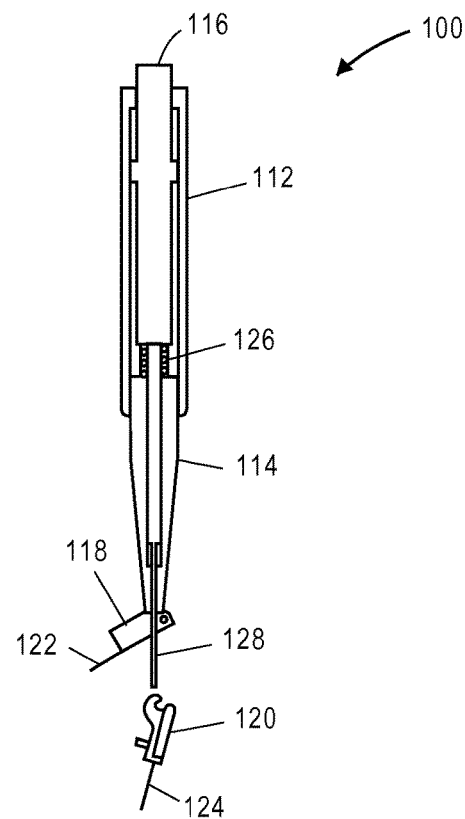

The distal end of apparatus 100 includes first portion 118 secured to moderate body 122. A second portion 120 is secured to minimal body 124 and is also detachably secured to first portion 118 around pin 134. The corneal implant (not shown in FIGS. 7 and 8 for clarity) is disposed between the moderate body and the minimal body in a nest formed by the moderate and minimal bodies. Second portion 120 is adapted to rotate with respect to first portion 118 around pin 134. FIG. 9 (sectional side view) illustrates the device after actuator 116 has been pressed down. When actuator 116 is pressed, spring 126 is compressed, and distal section 128 moves forward, or distally, through the channel in distal portion 114. The distal end of distal section 128 makes contact with second portion 120, forcing it downward as it rotates around pin 134. Because the corneal implant has a higher affinity for moderate body 122 than minimal body 124, the corneal implant will remain adhered to moderate body 122 as second portion 120 and minimal body 124 are rotated away from first portion 118 and moderate body 122. Once the curved portion of second portion 120 clears pin 134, second portion 120 is detached from first portion 118 and therefore from device 100, preparing the corneal implant for delivery (or, in some embodiments the corneal implant is delivered using a separate delivery device).

Figure 10:
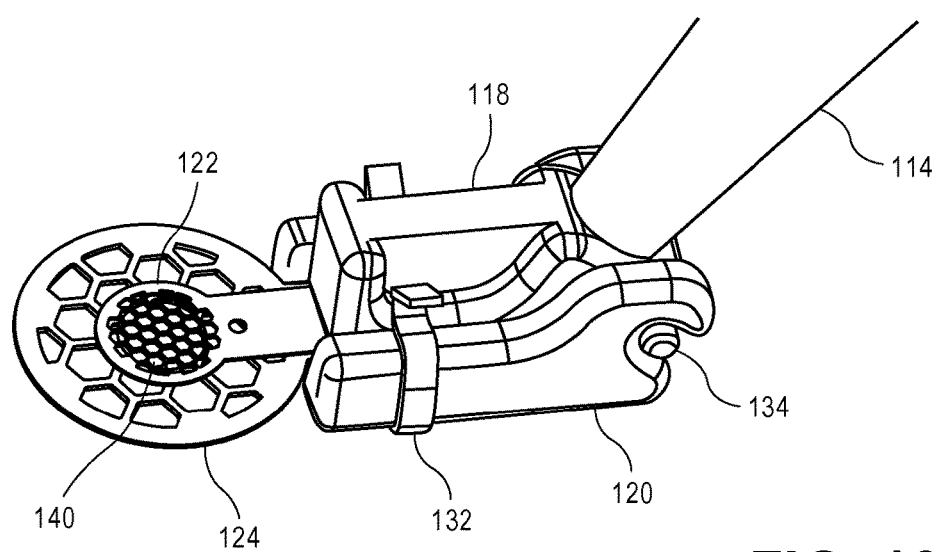

FIG. 10 illustrates a perspective view of the distal region of device 100. First portion 118 is secured to second portion 120 with clip 132, which is biased to the closed configuration shown in FIG. 10. Upon the application of the actuation force from actuator 116, clip 132 is forced into an open configuration, allowing second portion 120 and minimal body 124 to be rotated away from first portion 118.

Figure 11:
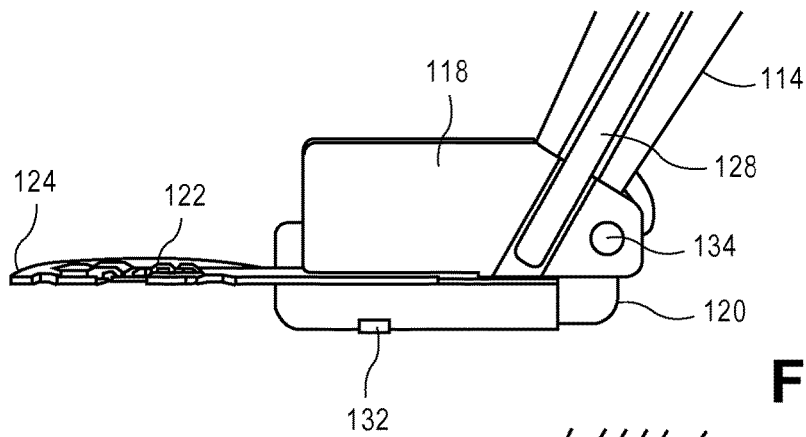
Figure 13:
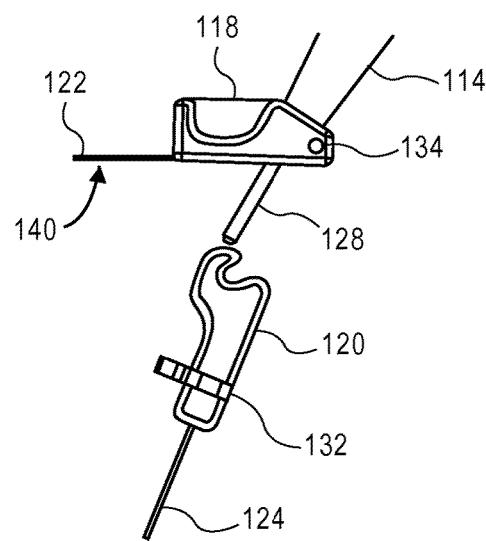

FIG. 11 illustrates a sectional side view of the distal portion of the device. FIG. 12 shows the sectional side view from FIG. 11 after actuator 116 has been actuated and second portion 120 is rotating away from first portion 118. Corneal implant 140 remains adhered to moderate body 122 due to the higher affinity of the moderate body. FIG. 13 illustrates a side view after second portion 120 has been completely disengaged from first portion 118. Actuator 116 is then released to cause distal section 128 to retract back into distal portion 114. Corneal implant 140 is now ready for delivery and can be delivered as described above. In some embodiments the corneal implant is positioned against stromal corneal tissue, and because the inlay has a higher affinity to the corneal tissue than to the moderate body, the inlay will disassociate from the moderate body and adhere to the corneal tissue.

FIGS. 14A-14D illustrate an exemplary embodiment of minimal and moderate bodies, which can be incorporated into the assembly from FIGS. 7-13. Minimal body 224 includes recess 225 formed therein such that when moderate body and minimal body are moved towards one another, they form a nest in which the inlay is retained (see FIG. 14D). The recess has a generally circular configuration (similar to the general configuration of minimal body 224), but other configurations may be suitable. Recess 225 is adapted to accommodate the corneal implant within the recess. Recess 225 is also sized to prevent inlay 140 (see FIGS. 14B-14D) from being compressed between the minimal and moderate bodies while being shipped or stored (see FIG. 14D). The corneal implant is therefore maintained in substantially unstressed, or non-deformed, configuration. Because the inlay has a defined curvature, it may be preferred to not allow the inlay to be distorted during shipping and/or storage, and the recess (and thus the nest) can be sized to help prevent it from being distorted. Additionally, because of the fluidic nature of some inlays, it can be difficult to constrain the inlay laterally between two parallel surfaces without the presence of a recess. The recess formed in the minimal body allows for easy containment without excess force being applied to the inlay. The nest formed by the moderate and minimal bodies prevents compression and/or damage to the inlay while acting as a storage compartment.

Figure 14A:
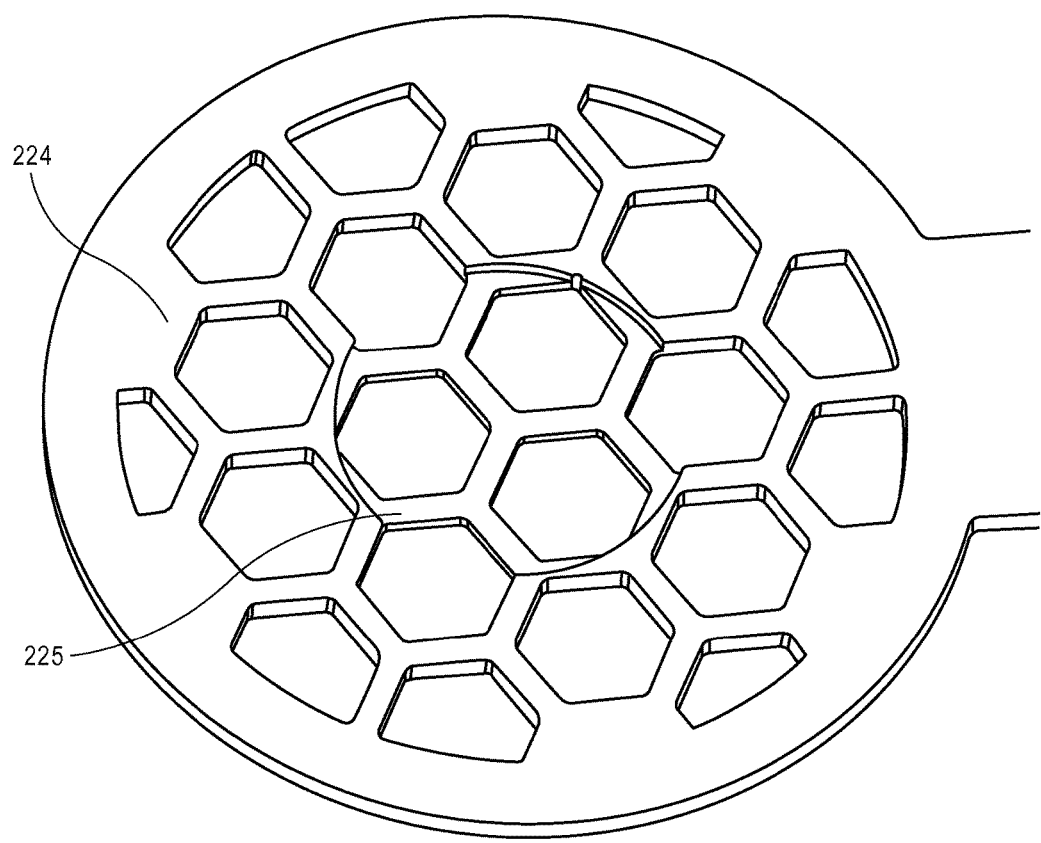
FIGS. 14A-19 illustrate exemplary moderate and minimal bodies.
Figure 14B:
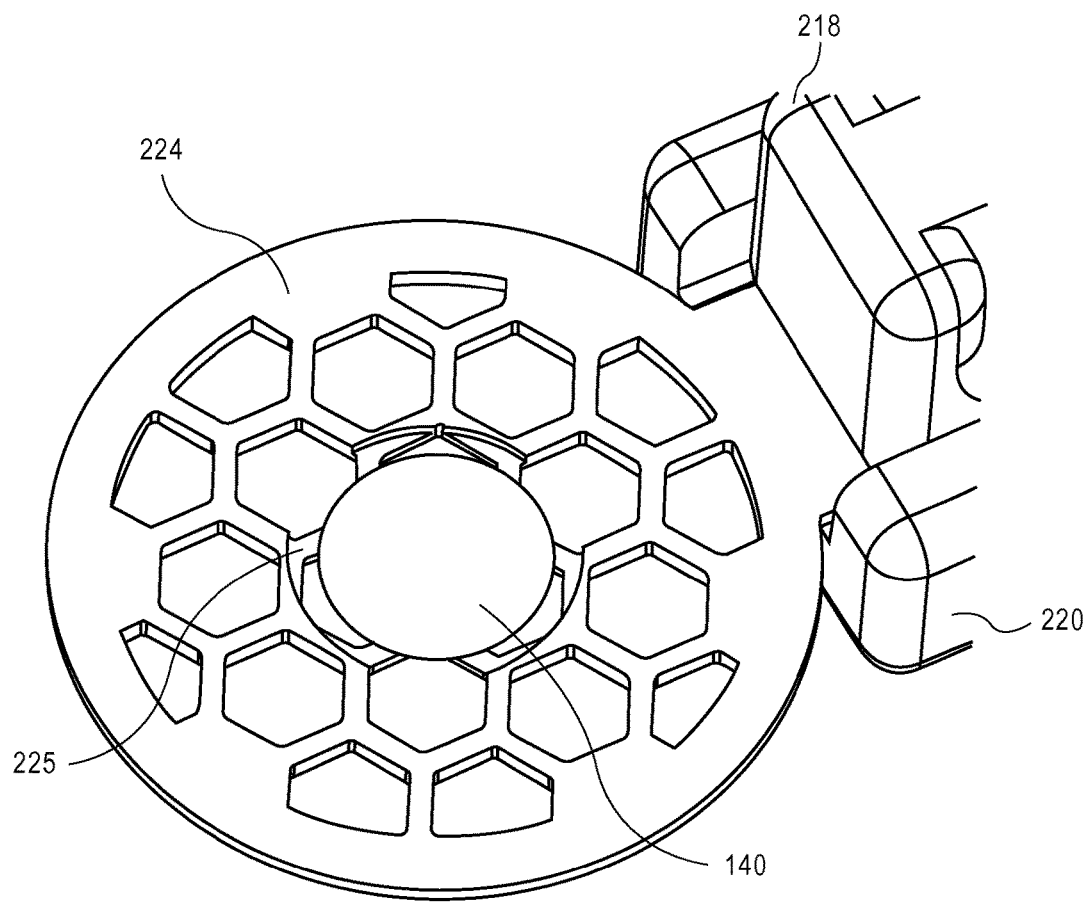
Figure 14C:
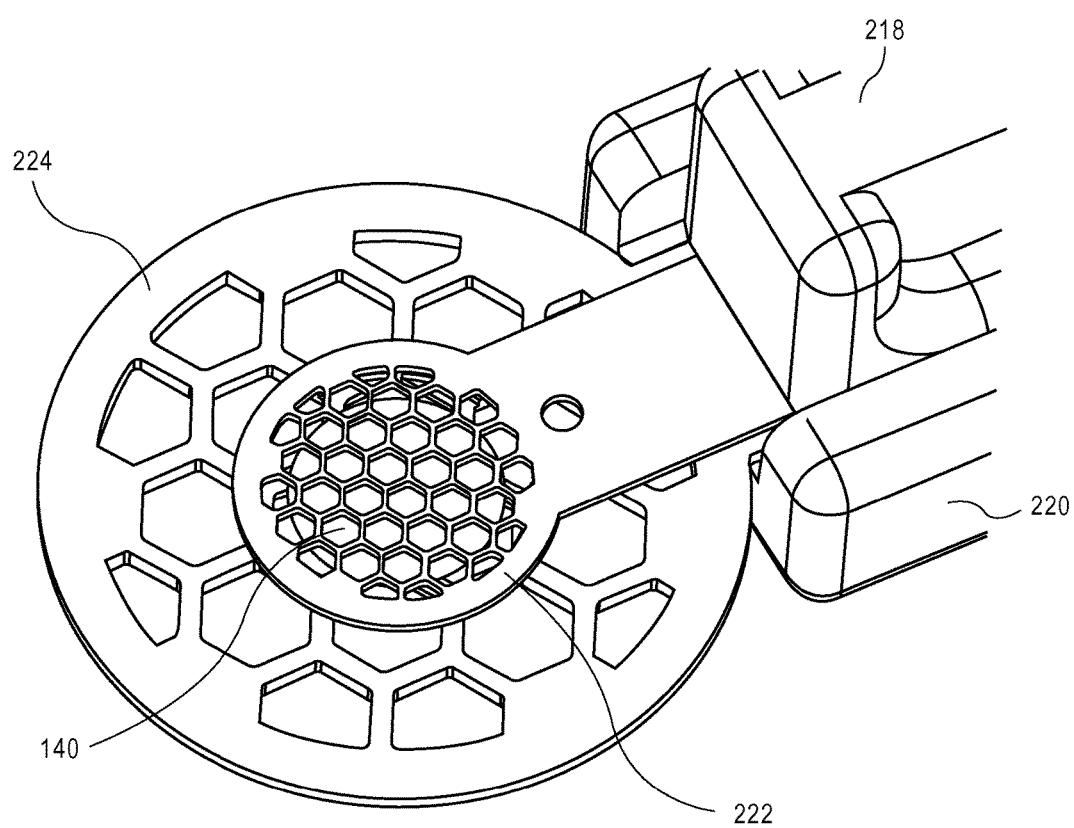
Figure 14D:
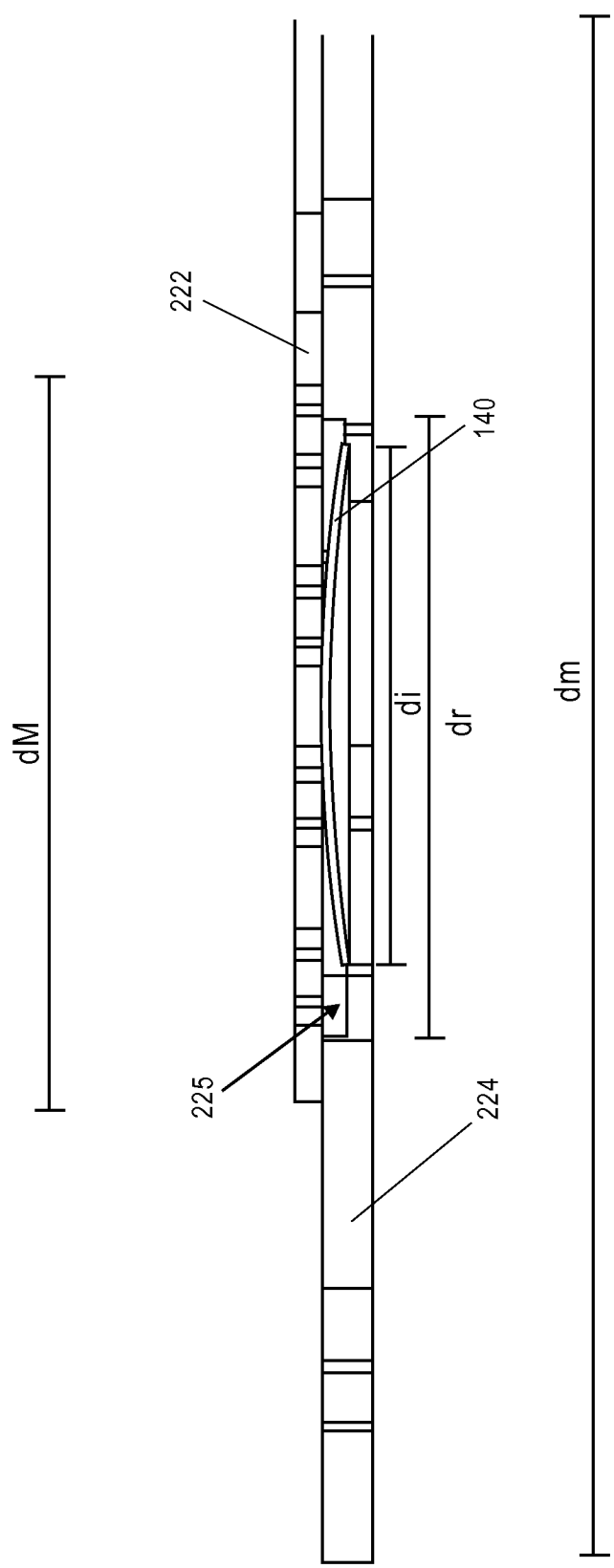

As can be seen in FIGS. 14B-14D, the recess size is larger than the inlay size. Particularly, in this embodiment, the diameter of the recess ("dr") is greater than the diameter of the inlay ("di"). Additionally, the diameter of the moderate body ("dM") is greater than the diameter of the recess ("dr") formed in the minimal body (see FIG. 14D). The diameter of the minimal body ("dm") is greater than the diameter of the moderate body ("dM").

The depth of the recess is greater than the material thickness of the inlay, but is preferably slightly less than the height of the corneal implant in a non-stressed configuration. This ensures that at least a portion of the corneal implant is maintained in contact with both the moderate body and the minimal body. If at least a portion of the corneal implant is not in contact with the moderate body, the corneal implant can remain adhered to the minimal body rather than the moderate body when the moderate and minimal bodies are moved away from one another. In an exemplary embodiment the material thickness of the corneal implant is about 38.1 microns, the overall height of the implant in a non-stressed configuration is about 152.4 microns, and the depth of the recess is between about 63.5 microns and about 114.3 microns.

Similar to the embodiment in FIGS. 7-13, moderate body 222 is secured to first portion 218, while minimal body 224 is secured to second portion 220. The system is used in the same manner as the embodiment in FIGS. 7-13.

In some exemplary embodiments of the systems shown herein (e.g., those in FIGS. 7-14D), the moderate body is stainless steel. In some embodiments it can be about 0.1 mm thick. As shown in the figures, the plurality of openings in the moderate body have general hexagon configurations. In some exemplary embodiments the dimension from a first side of the hexagon to a second side that is parallel to the first side (i.e., double the hexagon's apothem) of at least a substantial number of the hexagon shapes is about 0.35 mm. In some embodiments that dimension could be between about 0.02 mm to about 0.12 mm. The distance between hexagons (i.e., the distance from a first side of a first hexagon to a first side of a second hexagon, wherein the sides are parallel to one another and the hexagons are directly adjacent to one another) is about 0.05 mm, although this distance could be between about 0.01 mm and about 0.25 mm. The diameter of the moderate body can be about 3 mm, but in some embodiments it is between about 0.25 mm and about 13 mm. The above numerical limitations are merely exemplary and not intended to be limiting.

In some exemplary embodiments of the systems shown herein (e.g., those shown in FIGS. 7-14D), the minimal body is stainless steel, and is about 0.2 mm thick, except in the recess section. As shown in the figures, the openings in the minimal body each have general hexagon configurations. In some exemplary embodiments the dimension from a first side of the hexagon to a second side that is parallel to the first side (i.e., double the hexagon's apothem) of at least a substantial number of the hexagon shapes is about 1 mm. In some embodiments that dimension could be between about 0.1 mm to about 3 mm. The distance between hexagons (i.e., the distance from a first side of a first hexagon to a first side of a second hexagon, wherein the sides are parallel to one another and the hexagons are directly adjacent to one another) can be about 0.2 mm, although this distance could be between about 0.02 mm to about 0.12 mm. The diameter of the minimal body can be about 6.5 mm, but in some embodiments it is between about 3 mm and about 13 mm. The above numerical limitations are not intended to be limiting.

In some embodiments the diameter of the minimal body is at least about 2 times the diameter of the moderate body. In some embodiments the diameter of the minimal body is at least about 1.5 times the diameter of the moderate body. In some embodiments the size of the plurality of hexagons in the minimal body is at least about 2 times the size of the plurality of hexagons in the moderate body. In some embodiments they could be at least about 3 times, or at least about 4 times.

Figure 15:
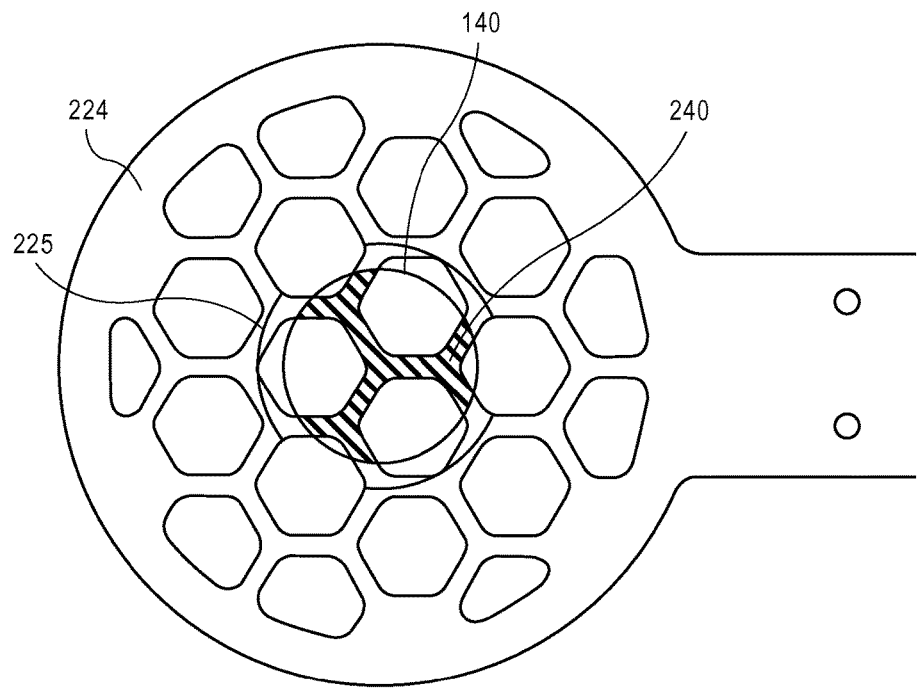
Figure 16:
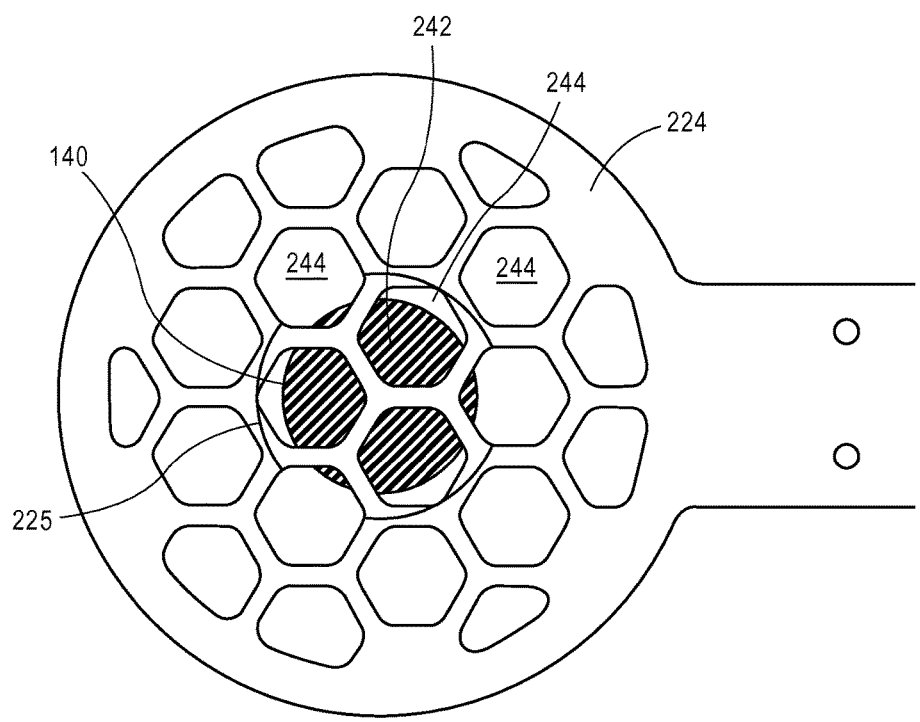

FIGS. 15-18 illustrate additional views illustrating the relative sizes and dimensions of the mesh bodies and a corneal inlay. In this embodiment the inlay has a diameter of about 2 mm. FIG. 15 is a top view illustrating minimal mesh body 224, recess 225 formed in minimal mesh body, periphery of inlay 140, and the surface area 240 (shown in hash lines) of minimal body 224 that overlaps with the inlay when the inlay is positioned in recess 225. In this particular embodiment surface area 240 of minimal body 224 that overlaps with the inlay is about 0.9 mm². The perimeter of the inlay that overlaps the minimal body is about 9 mm. FIG. 16 illustrates minimal mesh body 224 and periphery of inlay 140, and the surface area 242 (shown in hash lines) of openings 244 (only three openings 244 labeled) that overlaps the inlay when the inlay is in the recess. In this particular embodiment the surface area 242 is about 2 mm².

Figure 17:
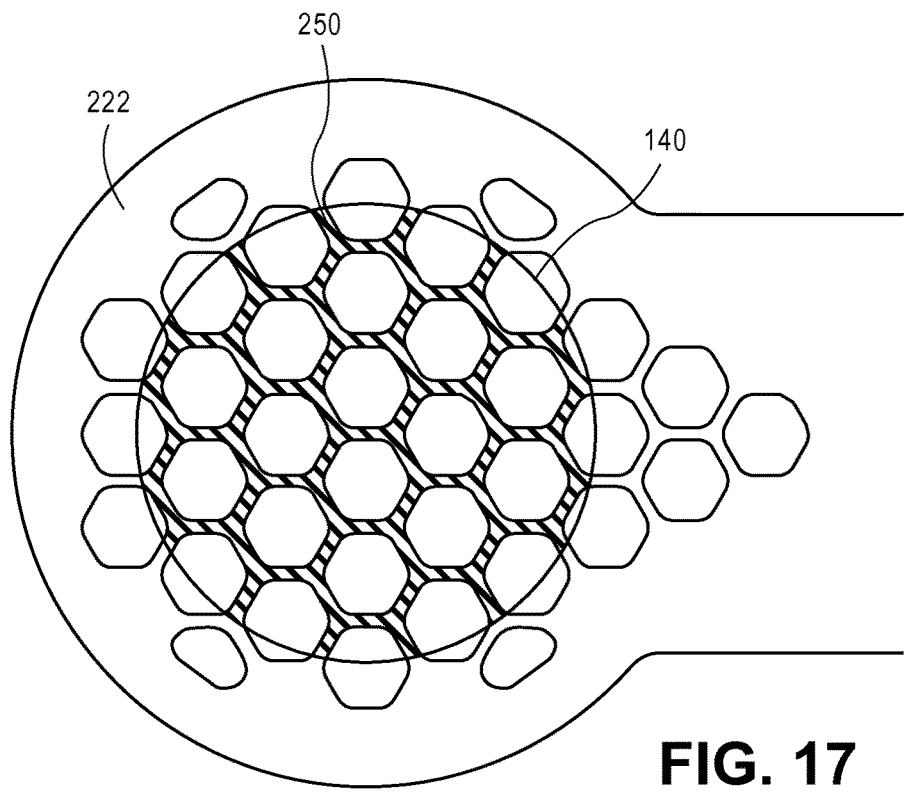
Figure 18:
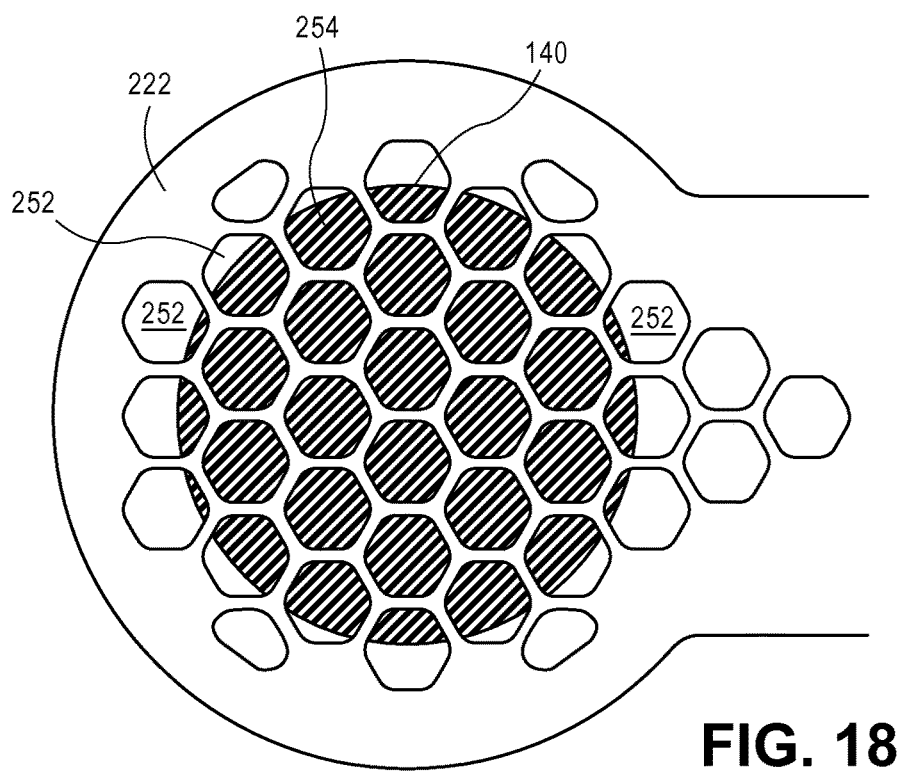

FIG. 17 illustrates moderate mesh body 222 and the periphery of inlay 140 disposed thereon. Surface area 250 of moderate body 222 is the surface area of the moderate body that overlaps the inlay, at least a portion of which is in contact with the inlay, when the inlay is positioned in the nest. In this particular embodiment surface area is about 0.75 mm². The perimeter of the inlay is about 26 mm. FIG. 18 illustrates moderate body 222, periphery of inlay 140, and the surface area 254 (shown in hash lines) of openings 252 (only three openings 252 are labeled) that overlap the inlay. Surface area 254 is about 2.3 mm².

In some embodiments the moderate body and the minimal body each have one or more openings, or apertures, extending through the bodies. The ratio of the moderate aperture perimeter (or sum of the aperture perimeters if more than one aperture) to the moderate aperture area (or sum of the apertures areas if more than one aperture) is greater than the ratio of the minimal aperture perimeter (or sum of the aperture perimeters if more than one aperture) to the minimal aperture area (or sum of the aperture areas if more than one aperture). Without necessarily wishing to be bound by a particular theory, the greater ratio results in greater forces being applied to the corneal implant from the moderate body than the minimal body, and thus provides the moderate body with a higher affinity for the corneal implant than the minimal body. When the moderate and minimal bodies are moved apart relative to one another, the greater forces applied to the implant will cause the implant to remain adhered to the moderate body rather than the minimal body.

By way of illustration only, in the embodiments shown in FIGS. 15-18, the sum of the perimeters of the apertures in the moderate body that overlap the implant were determined to be about 1.03 in, while the sum of the aperture areas that overlap the implant were determined to be about 0.0012 in². The ratio of perimeter to area for this particular moderate body was about 858 in$^{-1}$. The sum of the perimeters of the apertures in the minimal body that overlap the implant were determined to be about 0.365 in, while the sum of the aperture areas that overlap the implant were determined to be about 0.0014 in². The ratio of perimeter to area for this particular moderate body was about 260 in$^{-1}$. The ratio is therefore greater for the moderate body than for the minimal body.

Figure 19:
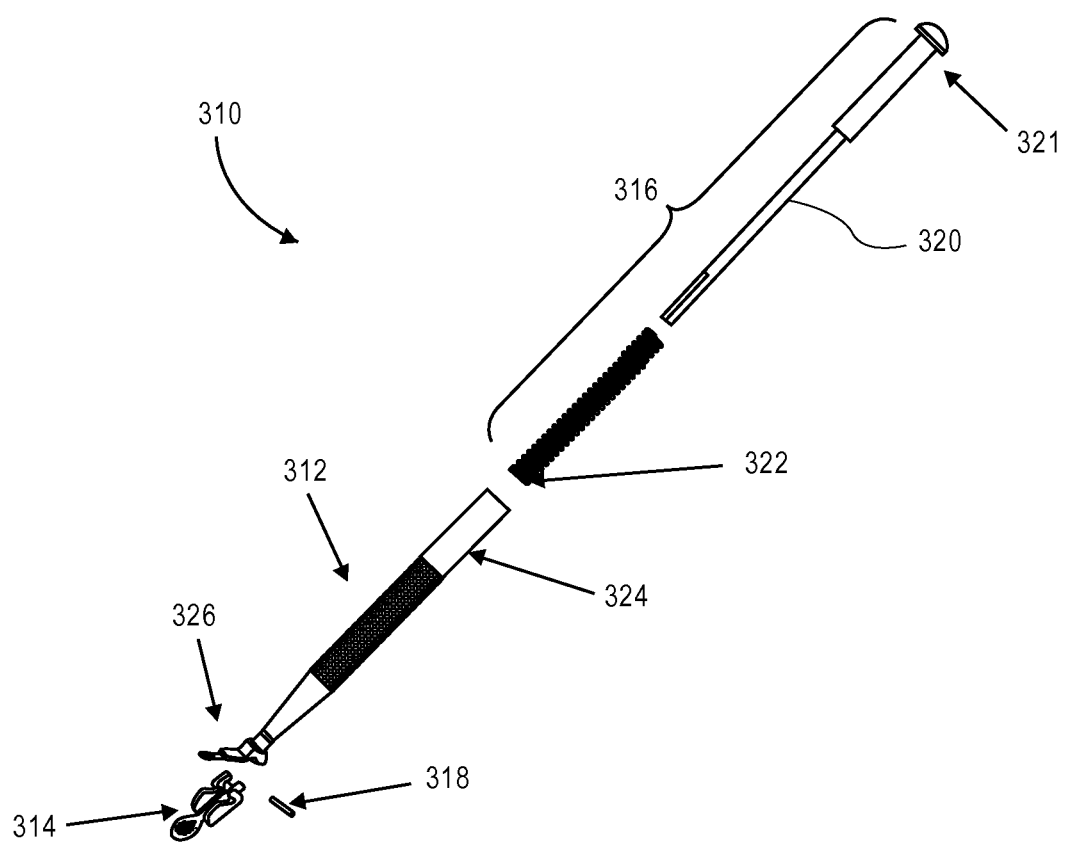

FIG. 19 is a partial exploded view of an exemplary corneal implant storage and positioning device. Positioning device 310 generally includes a handle assembly 312 that includes the moderate body, support assembly 314 that includes the minimal body, and actuator assembly 316 that is adapted to actuate, or move, support assembly 314 with respect to handle assembly 312. Due to the inlay's greater affinity for the moderate body, the inlay will adhere to the moderate body when the support assembly 314 is actuated.

Figure 20C:
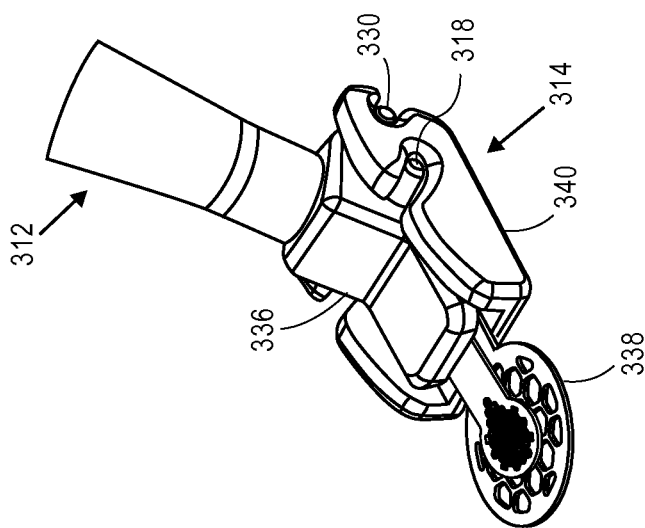
Figure 20B:
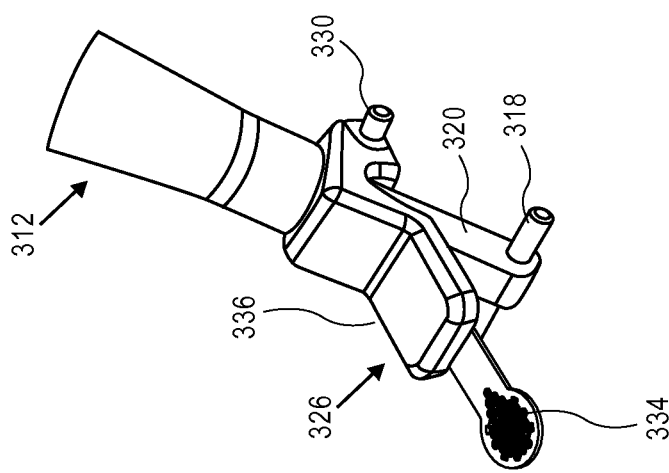
Figure 20A:
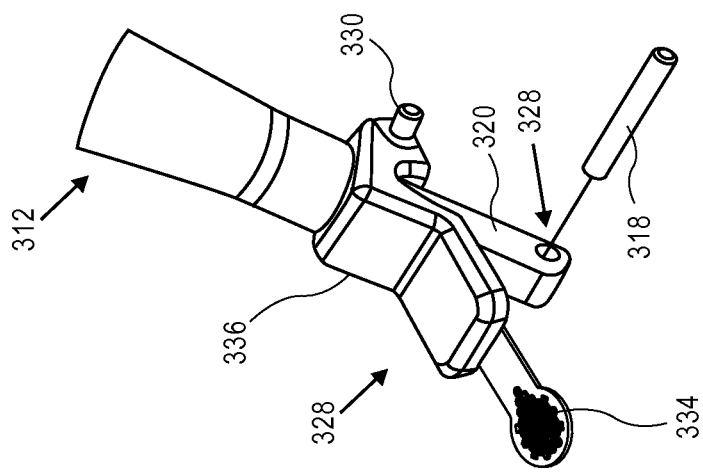

Actuator assembly 316 includes push rod 320 coupled to button 321, and spring 322. Handle assembly 312 includes handle 324 coupled to distal portion 326, which includes the moderate body. The distal end of spring 322 is secured within the internal channel within handle 312, and the proximal end of spring 322 is secured to the distal end of button 321. Push rod 320 is configured to be disposed within the internal lumen of spring 322. As shown in more detail in FIGS. 20A-20C, the distal end of push rod 320 includes bore 328 therethrough, adapted to receive dowel 318 therein. When push rod 320 has been advanced distally within handle assembly 312 and extends just out of the distal end of handle assembly 312, as shown in FIG. 20A, dowel 318 is advanced through bore 328. Dowel 318 both prevents push rod 320 from retracting proximally within handle assembly 312, but it also provides base assembly 314 with a surface to engage in order to secure support assembly 314 in place relative to handle assembly 312, as shown in FIG. 20C. The device also includes rod 330, which helps secure support assembly 314 in place relative to handle assembly 312 (see FIG. 20C), but allows support assembly 314 to rotate around rod 330 when the actuator is actuated. Dowel 318 is also involved in the actuation of the support assembly. Actuating button 321 causes push rod 320, and thus dowel 318, to be advanced distally within handle assembly 312. This causes dowel 318 to apply a generally distally directed force to support assembly 314, which causes dowel 318 to push down on support assembly 314. Upon the application of this force support assembly 314 will begin to rotate around rod 330, causing minimal body mesh 338 to move away from moderate mesh body 334. Further rotation of support assembly 314 will free support assembly 314 from rod 330, allowing support assembly 314 to be completely disengaged from handle assembly 312. Once disengaged, the corneal implant will remain adhered to moderate body 334 and is ready for use, such as delivery into or onto corneal tissue. Once the minimal mesh body is moved, the user can release button 321, and spring 322 causes actuator 316 to return to an at-rest, or non-actuated, position relative to handle assembly 312.

By incorporating rod 330, support assembly 314 rotates with respect to handle assembly 312 in only one direction, which prevents torqueing.

Figure 21:
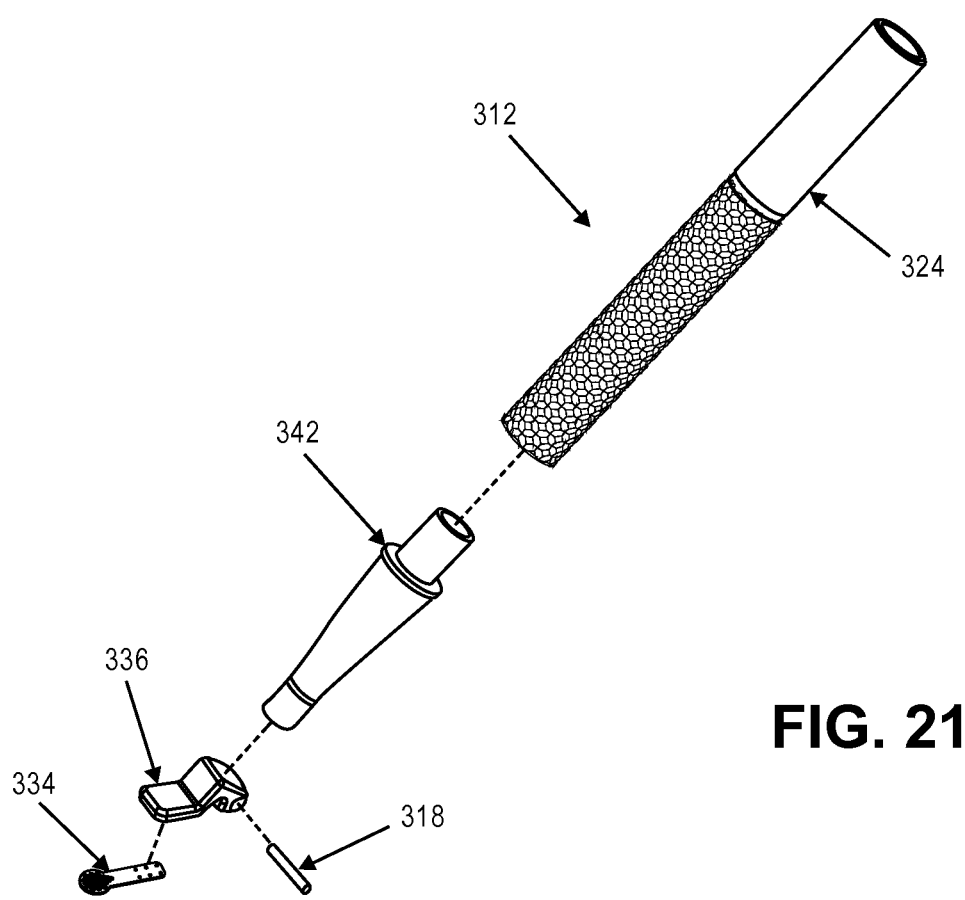
Figure 22:
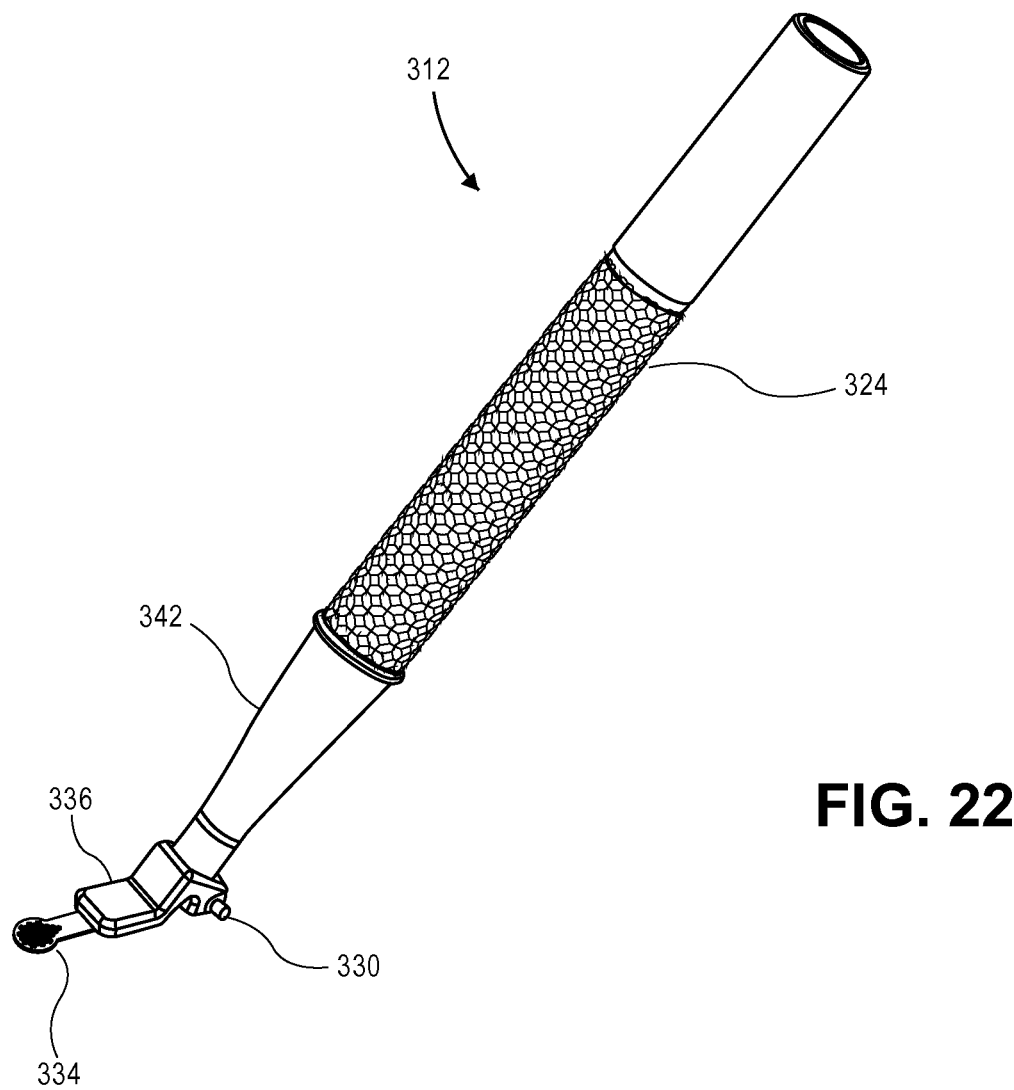
Figure 24I:
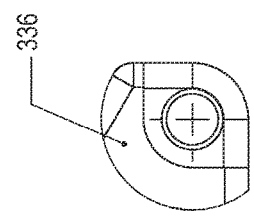
Figure 24H:
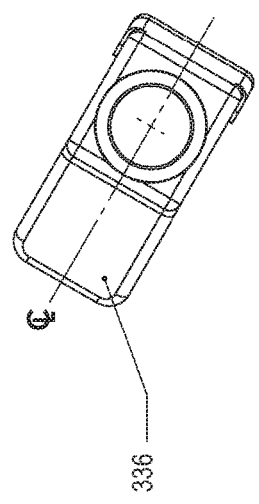
Figure 24G:
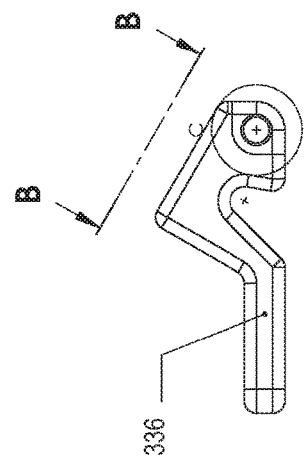

FIG. 21 is a partial exploded view of handle assembly 312 shown in FIG. 17 (actuator and base assembly not shown). Assembly 312 includes handle 324, distal tip portion 342, dowel 318, applicator base 336, and applicator 334. Handle 324 is secured to distal tip portion 342, and the distal end of distal tip portion 342 is disposed within a bore in applicator base 336. Applicator 334 is secured to applicator base 336. FIG. 22 shows the assembled view from FIG. 21.

FIGS. 23A-23D illustrate alternative views of the assembly of applicator base 336, applicator 334, and rod 330. FIG. 23A is an exploded perspective bottom view. FIG. 23B is a perspective top view illustrating how rod 330 is disposed within applicator base 336. FIG. 23C is a bottom view showing applicator 334 secured to applicator base 336 and a plurality of attachment points 350 for securing applicator 334 to applicator base 336. FIG. 23D is a front view showing applicator 34 secured to applicator base 336, and rod 330 disposed within applicator base 336. Applicator 334 and applicator base 336 can be secured together by any suitable technique. In one embodiment applicator 334 is welded to base 336, such as by resistance welding or laser welding. Applicator 334 includes the moderate mesh body.

FIGS. 24A-24I illustrate a variety of views of a particular embodiment of applicator base 336 described above. The internal bore through which the actuator extends can be seen in the sectional side view of FIG. 24D. The dimensions indicated in the figures are merely exemplary to this particular embodiment and are not limiting.

FIGS. 25A-25C illustrate exemplary dimensions for applicator 334, including the mesh dimensions, described above. For example, dimensions of the mesh that contribute to implant preference to adhere to the moderate body over the minimal body are shown. FIG. 25A is a top view. FIG. 25B is a side view. FIG. 25C is a detailed view of section A from FIG. 25A.

Figure 26A:
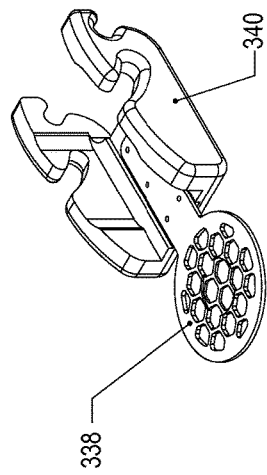
Figure 26B:
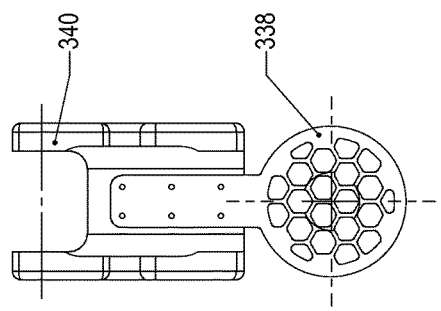
Figure 26C:
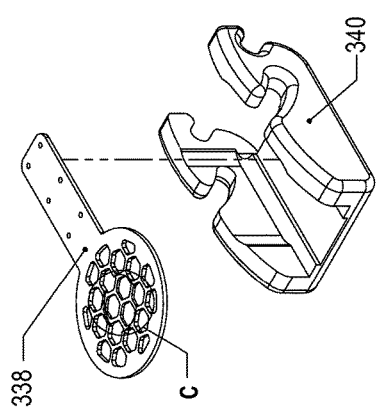
Figure 26D:
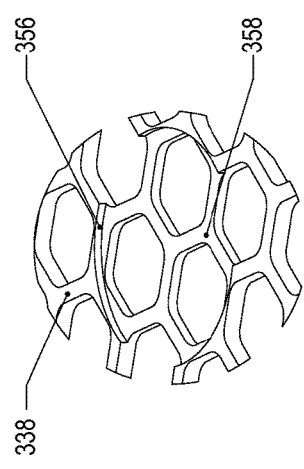
Figure 27D:
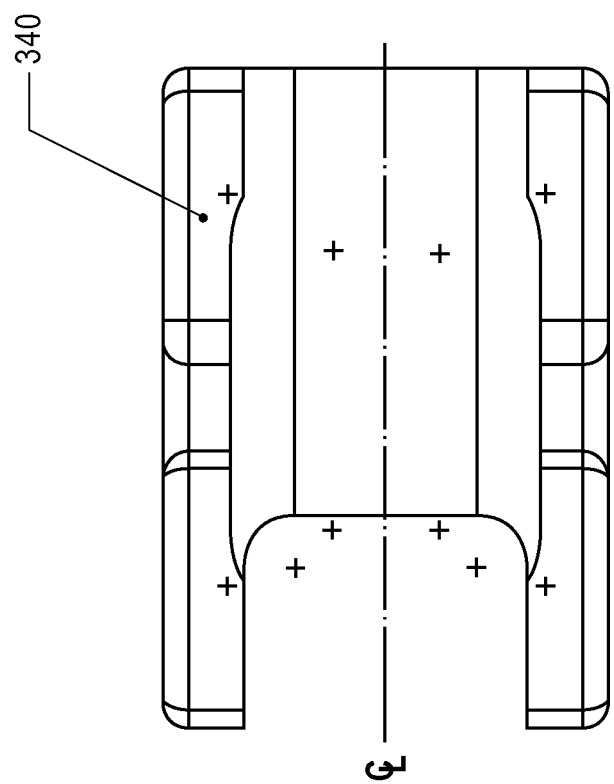

FIGS. 26A-26D illustrate support assembly 314 from FIG. 17, which includes support base 340 secured to implant support 338. Support base 340 and implant support 338 are secured to one another similarly to the applicator base and the applicator described above. FIG. 26A is an exploded view, while FIG. 26B is an assembled view. FIG. 26C is a top view. FIG. 26D is a detailed view C from FIG. 26A of applicator 338 showing recess 360 defined by recess sidewalls 356 and recess base surface 358. The implant is configured and sized to be disposed within the recess such that it is positioned between the minimal and moderate meshes prior to removal of the minimal body.

FIGS. 27A-27E illustrate front, sectional side, side, and top views of support base 340.

FIGS. 28A-28D illustrate views of the support 338. FIG. 28B illustrates section A-A shown in FIG. 28A. FIG. 28C shows detail B from FIG. 28B, and FIG. 28D shows detail C from FIG. 10A. Recess 360 is formed in a top portion of the support 338. Mesh apertures 364 are defined by body 362, illustrated in FIGS. 28B and 28C. The dimensions shown are exemplary and not intended to be limiting. The mesh apertures of the minimal body are larger than the mesh apertures of the moderate body, which is one of the contributing factors for why in this particular embodiment the implant preferentially adheres to the moderate body.

In general, the recess in the minimal mesh body should be sized to prevent forces, or a substantial amount of forces, from being applied to the corneal implant while it is positioned in the nest between the moderate and minimal bodies prior to use.

The mesh apertures and the recess can be created by any suitable technique, such as chemical etching, laser cutting, micro water jet cutting, etc. In some instances chemical etching provides for a cleaner cut and does not require as much post-manufacture processing of the body. The mesh apertures can be created from only one side, or in some embodiments half of the thickness of the aperture is created from one side, while the other half of the aperture is created from the other side. In some embodiments the recess is etched from one side, while the mesh apertures are created in the other side. Any combination or variation on these techniques can be used. In some embodiments the recess is created by plunge electrical discharge machining ("EDM").

In general, the net forces acting on the corneal implant are greater from the moderate mesh body than from the minimal mesh body. The polarity of water is an important factor when the corneal implant is formed of a hydrophilic material because in these instances the implant has properties like water and as such behaves like water. The dimensions of the mesh, configuration of the mesh, mesh body, and other factors can be modified to alter the relative affinities.

As described above, the minimal mesh body diameter is larger than the moderate mesh body diameter (both are shown to have a generally circular configuration). The minimal body diameter, due to its larger size, acts like a bumper, protecting the entire distal region of the apparatus during storage and use prior to actuation of the actuator. In the specific example shown above, the minimal body thickness is about twice as thick as the moderate body.

The moderate body diameter is larger than the recess, while the minimal body diameter is larger than the moderate body diameter. In some embodiments it may be helpful for the physician to be able to visualize the pupil when the corneal implant is being positioned in the cornea. For example, this may be desirable when implanting an inlay into the cornea wherein the inlay has a diameter less than the diameter of the pupil, such as a 1-3 mm diameter corneal inlay. For these applications the moderate mesh body can be sized such that it does not interfere with the visualization of the pupil. Specifically, the moderate mesh body portion is sized to allow the physician to be able to see the pupil during the delivery of the implant on corneal tissue. Starting with this constraint, the size of the other components can then be determined.

The use of "diameter" herein is not to suggest that the mesh body outer surfaces are perfectly circular or are circular at all. The two mesh portions could be square or rectangular-shaped, with the width and length of the minimal mesh portion larger than the width and length of the moderate mesh portion.

While in the embodiments above the implant's affinity for the moderate body is described as largely due to the size and configuration of the moderate mesh body relative to the minimal body, there are many ways to establish and control the implant's affinity for a given body. In some embodiments this can be accomplished by using a moderate body that is different than the minimal body. In some embodiments a finish could be applied to one or more of the surfaces of the moderate and minimal bodies. The finish can be different on the moderate and the minimal body to control the preferential adhesion. In some embodiments the moderate body has a better finish than the minimal body. In some embodiments the minimal body has a matte finish on it.

One or more components of the devices described herein can be a stainless steel or titanium. For example, applicator base 36 and applicator 34 can both be stainless steel, one can be titanium while the other is stainless steel, or both can be titanium.

Figure 29B:
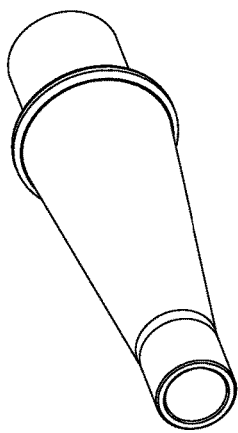
Figure 29C:
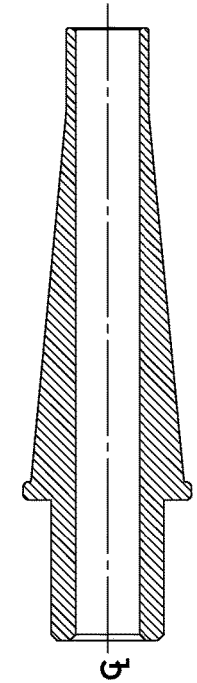
Figure 29A:
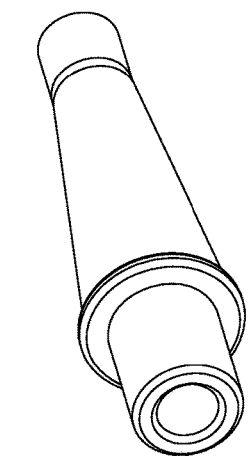
Figure 29D:
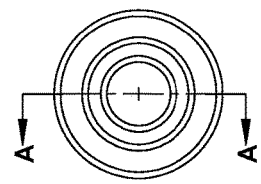

FIGS. 29A-29D illustrate views of distal tip 342 from the handle assembly described above. FIG. 29A is a view looking from the proximal end to the distal end, FIG. 29B is a view from the distal end to the proximal end, FIG. 29C is a sectional side view, and FIG. 29D is a front view. The distal tip is secured to the handle, and the distal end of it is disposed in the applicator base 336.

Figure 30D:
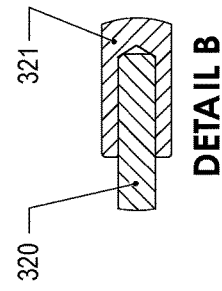
Figure 30B:
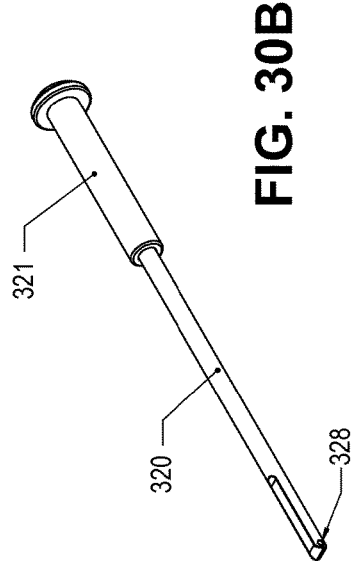
Figure 30E:
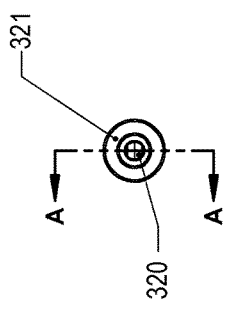
Figure 30C:
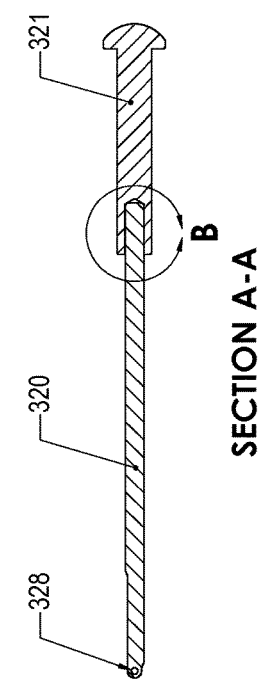
Figure 30A:
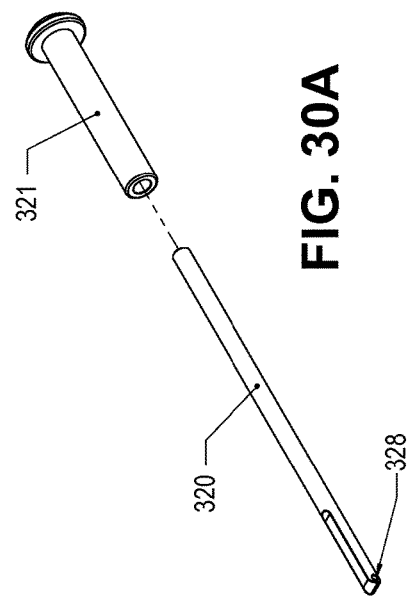
Figure 31B:
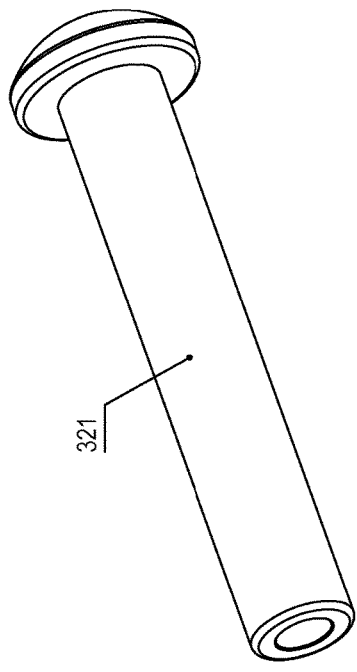
Figure 31A:
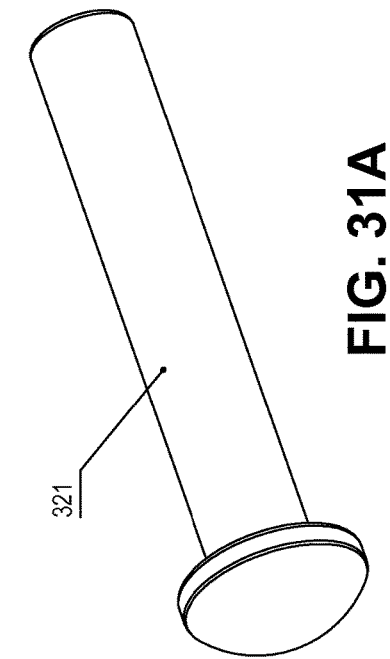
Figure 31D:
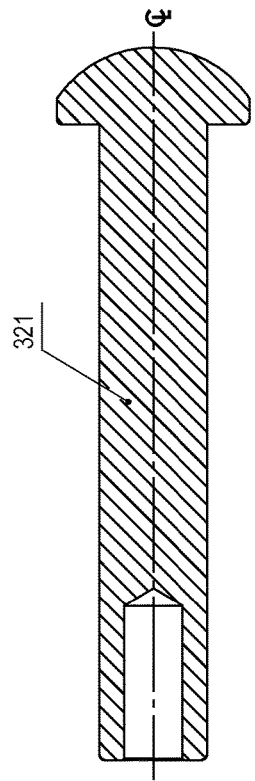
Figure 31C:
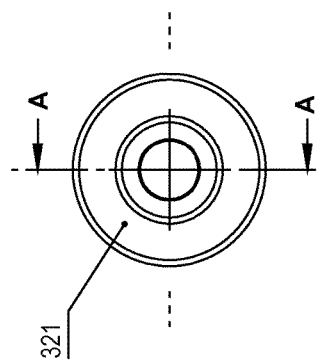
Figure 32A:
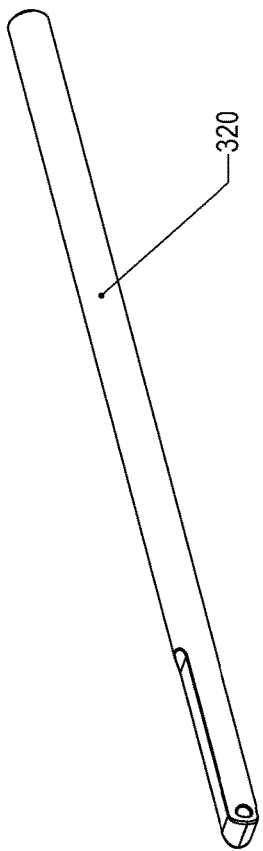
Figure 32B:
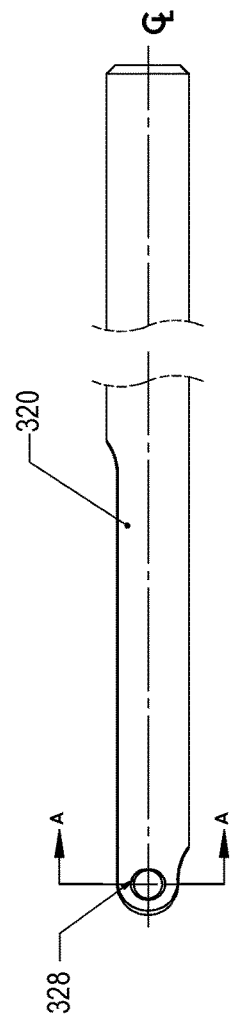
Figure 32C:
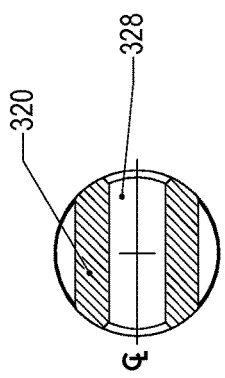
Figure 32D:
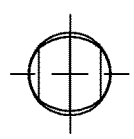
Figure 33A:
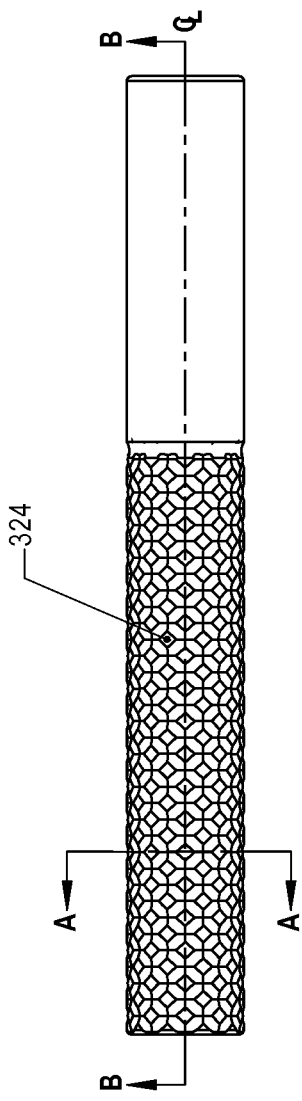
Figure 33A:
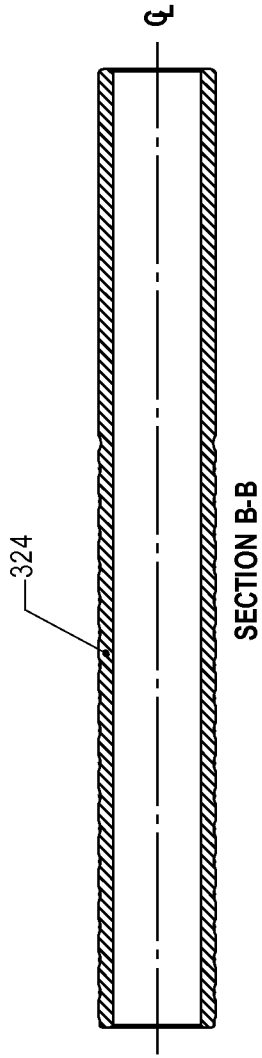
Figure 33A:
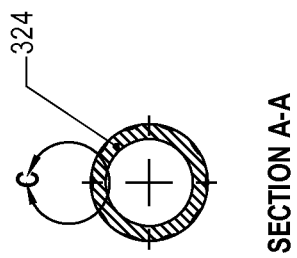
Figure 33A:
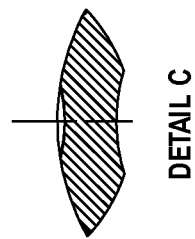

FIGS. 30A-30E illustrate in detail actuator assembly 316 from FIG. 19. The actuator includes button 321, push rod 320, and bore 328 at the distal end of push rod 320. FIG. 30A is an exploded view, FIG. 30B is an assembly view, FIG. 30C is a side sectional view of section A-A shown in FIG. 30E, and FIG. 30D is a detail view of section B shown in FIG. 30C.

FIGS. 31A-31D illustrate detailed views of button 321. FIGS. 32A-32D illustrate detailed views of push rod 320, including bore 328.

Figure 34A:
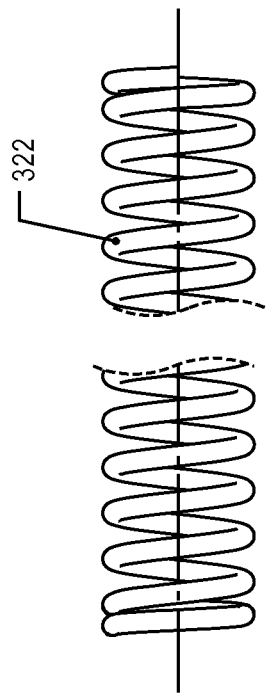
Figure 34B:
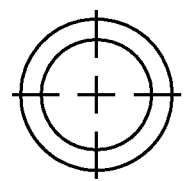
Figure 35A:
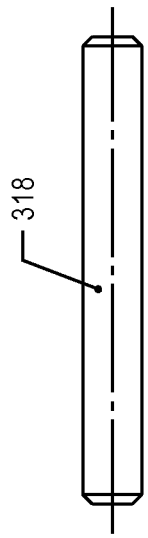
Figure 35B:
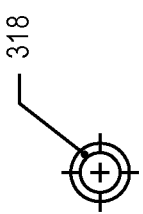

FIGS. 33A-33D illustrate detailed views of handle 324. FIGS. 34A and 34B illustrate detailed views of spring 322. FIGS. 35A and 35B illustrate detailed viewed of dowel 18.

Once the corneal implant is loaded in the apparatus between the moderate and minimal bodies, the implant can be used right away or it can be stored in packaging for any suitable period of time. When the corneal implant is made of a hydrogel material, it is important to keep the implant adequately hydrated during storage.

Embodiments herein describe both a moderate body and a minimal body. In some embodiments, however, the apparatus or its method of use need not include the minimal body. Without the minimal body, the corneal implant is not positioned within a corneal nest defined by the moderate and minimal bodies. The implant therefore need not be packaged with the moderate body. For example, it can be packaged in a separate packaging. In these embodiments the moderate body can utilize its preferential adhesion for the implant as set forth above to retrieve, or pick up, the corneal implant from its packaging. This can eliminate restrictions on how the cornel implant needs to be packaged. For example, the implant can be stored in a vial, free-floating in a storage medium. When the implant is ready to be positioned on the corneal tissue, the moderate body, which can be coupled to a handle, is positioned adjacent the implant in its storage medium, such as by scooping up the corneal implant into a position adjacent the apertures therein. Due to its preferential adhesion adaptation, the corneal implant will preferentially adhere to the moderate body. Once it has adhered to the moderate body, the implant is ready to be deposited onto the cornea as set forth above by relying on the moderate body's adaptation to allow the implant to preferentially adhere to the corneal tissue rather than the moderate body.

What is claimed is:

1. A corneal implant applicator apparatus, comprising
a corneal implant applicator comprising a corneal implant applicator surface with at least one opening therethrough;
a corneal implant support disposed relative to the corneal implant applicator, the corneal implant support having a corneal implant support upper surface and a corneal implant support lower surface, wherein the upper and lower surfaces have a therethrough;
a corneal implant disposed between the corneal implant applicator and the corneal implant support,
wherein the corneal implant applicator surface and the corneal implant support surface are adapted such that the corneal implant preferentially adheres to the corneal implant applicator surface rather than the corneal implant support surface when the corneal implant support is moved relative to the corneal implant applicator due to the corneal implant's preference for adhering to the corneal implant applicator surface rather than the corneal implant support surface, and such that the corneal implant preferentially adheres to corneal tissue rather than the corneal implant applicator surface when the corneal implant applicator is moved relative to the corneal tissue due to the corneal implant's preference for adhering to the corneal tissue rather than the corneal implant applicator surface.

2. The apparatus of claim 1 wherein the corneal implant support is adapted to be moved relative to the applicator to provide access to the corneal implant and cause the corneal implant to preferentially adhere to the corneal implant applicator.

3. The apparatus of claim 1 wherein the corneal implant comprises a hydrophilic material.

4. The apparatus of claim 1 wherein the corneal implant support is disposed relative to the corneal implant applicator to form a corneal implant chamber.

* * * * *